(12) United States Patent
Gong et al.

(10) Patent No.: US 12,398,370 B2
(45) Date of Patent: Aug. 26, 2025

(54) CULTURE MEDIUM AND METHOD FOR INDUCING IPSC DIFFERENTIATION TO OBTAIN MACROPHAGES AND USE THEREOF

(71) Applicant: ALLIFE MEDICINE (BEIJING) LIMITED, Beijing (CN)

(72) Inventors: Shixin Gong, Beijing (CN); Yuchun Gu, Beijing (CN); Nan Li, Beijing (CN); Qinqing Peng, Beijing (CN); Lida Wu, Beijing (CN)

(73) Assignee: ALLIFE MEDICINE (BEIJING) LIMITED, Beijing (CN)

( * ) Notice: Subject to any disclaimer, the term of this patent is extended or adjusted under 35 U.S.C. 154(b) by 0 days.

(21) Appl. No.: 19/053,424

(22) Filed: Feb. 14, 2025

(65) Prior Publication Data

US 2025/0179434 A1    Jun. 5, 2025

Related U.S. Application Data

(63) Continuation of application No. PCT/CN2023/089111, filed on Apr. 19, 2023.

(30) Foreign Application Priority Data

Aug. 15, 2022 (CN) .......... 202210974483.X

(51) Int. Cl.
  *C12N 5/00* (2006.01)
  *C12N 5/0786* (2010.01)

(52) U.S. Cl.
  CPC ........ *C12N 5/0645* (2013.01); *C12N 2500/02* (2013.01); *C12N 2500/25* (2013.01); *C12N 2500/32* (2013.01); *C12N 2500/38* (2013.01); *C12N 2500/44* (2013.01); *C12N 2500/50* (2013.01); *C12N 2501/052* (2013.01); *C12N 2501/115* (2013.01); *C12N 2501/125* (2013.01); *C12N 2501/15* (2013.01); *C12N 2501/155* (2013.01); *C12N 2501/165* (2013.01); *C12N 2501/22* (2013.01); *C12N 2501/2303* (2013.01); *C12N 2501/2305* (2013.01); *C12N 2501/2313* (2013.01); *C12N 2501/24* (2013.01); *C12N 2501/727* (2013.01); *C12N 2506/45* (2013.01); *C12N 2523/00* (2013.01); *C12N 2533/52* (2013.01); *C12N 2533/54* (2013.01)

(58) Field of Classification Search
  CPC .................................................. C12N 5/0645
  See application file for complete search history.

(56) References Cited

U.S. PATENT DOCUMENTS

| | | | |
|---|---|---|---|
| 2018/0010096 A1 | 1/2018 | Lim et al. | |
| 2020/0297763 A1 | 9/2020 | Zhang et al. | |
| 2022/0211757 A1* | 7/2022 | Yang .................. | C07K 14/7051 |

FOREIGN PATENT DOCUMENTS

| | | | |
|---|---|---|---|
| CN | 106867961 A | | 6/2017 |
| CN | 109082411 | * | 12/2018 |
| CN | 109082411 A | | 12/2018 |
| CN | 109913494 A | | 6/2019 |
| CN | 109971709 A | | 7/2019 |
| CN | 110607277 A | | 12/2019 |
| CN | 111321110 A | | 6/2020 |
| CN | 113462638 A | | 10/2021 |
| CN | 113832104 | * | 12/2021 |
| CN | 113832104 A | | 12/2021 |
| CN | 114774365 A | | 7/2022 |
| CN | 202210677254 | * | 7/2022 |
| CN | 115433715 A | | 12/2022 |
| WO | 2019117444 A1 | | 10/2018 |
| WO | 2020106215 A1 | | 5/2020 |

OTHER PUBLICATIONS

Huang, Minin et al., Immunoregulatory effect of mesenchymal stem cell via mitochondria signaling pathways in allergic asthma, Saudi Journal of Biological Sciences, 28(12): 6957-6962, 2021.
International Search Report in PCT/CN2023/089111 mailed on Aug. 21, 2023, 8 pages.
Written Opinion in PCT/CN2023/089111 mailed on Aug. 21, 2023, 8 pages.
Cao, Xu et al., Differentiation and Functional Comparison of Monocytes and Macrophages from hiPSCs with Peripheral Blood Derivatives, Stem Cell Reports, 12: 1282-1297, 2019.
Zhang, Li et al., Pluripotent stem cell-derived CAR-macrophage cells with antigen-dependent anti-cancer cell 5 functions, Journal of Hematology & Oncology, 2020, 5 pages.
First Office Action in Chinese Application No. 202210974483.X mailed on Mar. 1, 2023, 10 pages.
Notification to Grant Patent Right for Invention in Chinese Application No. 202210974483.X mailed on Mar. 26, 2023, 4 pages.

* cited by examiner

*Primary Examiner* — James D Schultz
*Assistant Examiner* — Keenan A Bates
(74) *Attorney, Agent, or Firm* — Porus IP LLC

(57) ABSTRACT

A medium combination and a method for inducing iPSC differentiation to obtain macrophages and use thereof are provided. The medium combination includes a first stage medium to a sixth stage medium. The first stage medium is an E8 complete medium containing a ROCK pathway inhibitor and polyvinyl alcohol, the second stage medium is an E8 complete medium containing a GSK-3β inhibitor, the third stage medium includes an M1 medium and an M2 medium, the fourth stage medium is an M3 medium, the fifth stage medium is an M4 medium, and the sixth stage medium is an M5 medium.

3 Claims, 24 Drawing Sheets

Day 26

CULTURE MEDIUM AND METHOD FOR INDUCING IPSC DIFFERENTIATION TO OBTAIN MACROPHAGES AND USE THEREOF

CROSS-REFERENCE TO RELATED APPLICATIONS

This application is a continuation of international application No. PCT/CN2023/089111, filed Apr. 19, 2023, which claims priority to Chinese patent application No. 202210974483.X, filed on Aug. 15, 2022, the entire contents of each of which are incorporated herein by reference.

TECHNICAL FIELD

The present disclosure relates to the field of biomedical technology, and in particular, to a culture medium and a method for inducing iPSC differentiation to obtain macrophages and use thereof.

BACKGROUND

Macrophages are key components of the innate immune system, which are distributed in a variety of tissues and organs. Macrophages are involved in both nonspecific defense (innate immunity) and specific defense (cellular immunity). Macrophages play a role in clearing bacterial, viral, and fungal pathogens in nonspecific immunity, and antigen presentation and production of appropriate cytokines in the specific immune response. Macrophages, as a population of cells with plasticity and pluripotency, exhibit significant functional differences under the influence of different microenvironments in vivo and in vitro. Currently, according to the different activation states and functions, macrophages may be mainly classified into M1 macrophages, i.e., classically activated macrophages, and M2 macrophages, i.e., alternatively activated macrophages. In addition, macrophages are cells with multiple differentiation sources, for example, monocytes, CD34+ hematopoietic stem cells, early T-lymphocytes, etc. can be differentiated into macrophages under certain conditions.

Currently, there are two main sources of human macrophages used in in vitro experiments, one is tumor-derived cell lines such as U937 and THP 1, and the other is primary cells such as macrophages derived from peripheral blood monocytes. Macrophages derived from tumor-derived cell lines have unlimited proliferative potential which plays an important role in macrophage-related biological studies, but compared with primary macrophages, these derivatized cell lines are prone to non-normal genetic structural changes, leading to functional deficits. However, although macrophages derived from peripheral blood are relatively easy to obtain, they are unable to self-renew, lack proliferative capacity, and are more difficult to genetically edit, resulting in unrepresentative test results.

Induced pluripotent stem cells (iPSC) are capable of inducing differentiation into macrophages in vitro. Macrophages generated by iPSC induction have received widespread attention due to the advantages of abundant sources, relatively easy acquisition, and the ability to obtain individual-specific iPSCs. However, the mechanism of iPSC differentiation to macrophages is unclear and the efficiency of induction is low. Currently, there are two main ways to induce macrophage differentiation, including monolayer adhesion induction and the formation of embryoid bodies (EBs). Cao et al (Differentiation and Functional Comparison of Monocytes and Macrophages from hiPSCs with Peripheral Blood Derivatives) disclose obtaining suspended hematopoictic stem cells by monolayer adherent induction, followed by further induction to obtain monocytes, and further induction of macrophage differentiation. This scheme has a yield of approximately 36.83±10.40 monocytes obtained from 1 iPSC and a cycle for obtaining monocytes of 15 days, and macrophages are obtained after further differentiation for 7 days. However, the complex cytokines used in this scheme and the low induction yield are not conducive to a large-scale induction strategy. Zhang et al. (Pluripotent stem cell-derived CAR-macrophage cells with antigen-dependent anti-cancer cell functions) disclose that macrophages are prepared using the manner of formation of EBs, and EBs are attached to a culture plate coated with matrigel after 10 days of iPSC induction and continued to be cultured until day 27 to obtain macrophages. The yield of the scheme is about 50 macrophages obtained from 1 iPSC, but the medium formulation of this scheme is complicated and the yield is low. CN109082411B discloses a method for obtaining macrophages with phagocytosis by differentiation of pluripotent stem cells, with a complex formulation of medium and a high cost, the method includes inducing the iPSC to gradually form EBs, mesangial cells, hematopoietic cells, myeloid cells, macrophages, and mature macrophages, and the whole process lasting 29 days, but the last medium of the scheme uses fetal bovine serum, which introduces exogenous substances.

There is therefore an urgent need to develop an efficient, stable, and low-cost medium and method for inducing iPSC differentiation to obtain macrophages. In addition, the applicant has applied for the Chinese patent application No. CN202210677254.1, titled as a method for inducing iPSC differentiation to obtain CD34+ cells and NK cells and use thereof.

SUMMARY

One or more embodiments of the present disclosure provide a medium combination for inducing iPSC differentiation to obtain macrophages, comprising a first stage medium, a second stage medium, a third stage medium, a fourth stage medium, a fifth stage medium, and a sixth stage medium.

The first stage medium is an E8 complete medium containing a ROCK pathway inhibitor and polyvinyl alcohol, the second stage medium is an E8 complete medium containing a GSK-3β inhibitor, the third stage medium comprises an M1 medium and an M2 medium, the fourth stage medium is an M3 medium, the fifth stage medium is an M4 medium, and the sixth stage medium is an M5 medium.

The M1 medium comprises a stempro-34 complete medium, DMEM/F12, L-glutamine, ascorbic acid, Insulin-Transferrin-Selenium-Ethanolamine, BMP4, VEGF, and bFGF, and the M2 medium comprises the M1 medium and inhibitors of TGF-β type I receptors ALK5, ALK4, and ALK7.

The M3 medium comprises X-VIVOTM 15, L-glutamine, ascorbic acid, Insulin-Transferrin-Selenium-Ethanolamine, NEAA, β-mercaptocthanol, BMP4, VEGF, bFGF, SCF, IL-3, and M-CSF.

The M4 medium comprises X-VIVOTM 15, L-glutamine, ascorbic acid, Insulin-Transferrin-Selenium-Ethanolamine, NEAA, β-mercaptoethanol, IL-3, and M-CSF.

The M5 medium comprises X-VIVOTM 15, L-glutamine, ascorbic acid, Insulin-Transferrin-Selenium-Ethanolamine, NEAA, β-mercaptoethanol, and M-CSF.

BRIEF DESCRIPTION OF THE DRAWINGS

This disclosure is further illustrated by way of exemplary embodiments, which is described in detail by the accompanying drawings. These embodiments are not limiting, and in these embodiments, the same numbering denotes the same structure, wherein.

DETAILED DESCRIPTION

Figure 1:
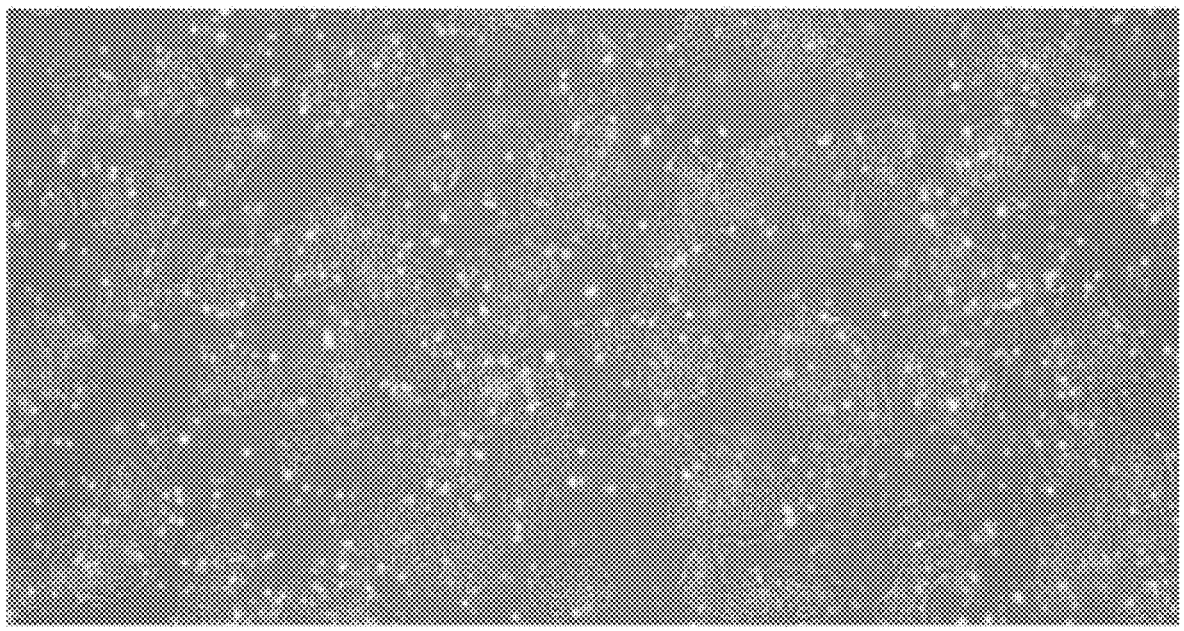
FIG. 1 is a cell morphology image of iPSC cells under a 4× optical microscope according to some embodiments of the present disclosure.

In order to more clearly illustrate the technical solutions of the embodiments of the present disclosure, the accompanying drawings required to be used in the description of the embodiments are briefly described below. Obviously, the accompanying drawings in the following description are only some examples or embodiments of the present disclosure, and it is possible for a person of ordinary skill in the art to apply the present disclosure to other similar scenarios in accordance with these drawings without creative labor. Unless obviously obtained from the context or the context illustrates otherwise, the same numeral in the drawings refers to the same structure or operation.

As shown in the disclosure and the claims, unless the context clearly suggests an exception, the words "a", "an", and/or "the" do not refer specifically to the singular, but may also include the plural. Generally, the terms "including" and "comprising" suggest only the inclusion of clearly identified steps and elements that do not constitute an exclusive list, and the method or apparatus may also include other steps or elements.

All technical and scientific terms used herein have the meanings commonly understood by those of ordinary skill in the art, unless otherwise indicated. In order to further explain the present disclosure, some of the terminology involved in the present disclosure is explained as follows.

As used herein, "stem cell" means an undifferentiated or insufficiently differentiated cell that is capable of, on the one hand, self-renewing, i.e., producing more cells identical to itself, and on the other hand, differentiating into two or more mature cell types. According to the source of stem cells, stem cells are categorized into embryonic stem cells (ES cells) and adult stem cells. Embryonic stem cells may be derived from early animal embryos such as the inner cell mass of blastocysts (i.e., early embryos), which have the ability to differentiate into every cell type in the body (totipotency). Adult stem cells are found in various organs and tissues of the adults and have the ability to differentiate and replace cells in their tissues (pluripotency). Hematopoietic stem cells (HSC) are adult stem cells, which are found in the bone marrow and have the ability to differentiate into various blood cells. Hematopoietic stem cells (HSC) are capable of producing both myeloid and lymphoid progenitor cells, and further producing myeloid cells (e.g., monocytes, macrophages, neutrophils, basophils, dendritic cells, erythrocytes, platelets, etc.) and lymphoid cells (e.g., T cells, B cells, NK cells, etc.). The ability of stem cells to self-replicate and differentiate into multiple or specific cell types makes them central to cellular replacement therapies.

As used herein, "induced pluripotent stem cell (iPSC)" refers to stem cells with totipotency or pluripotency obtained from certain adult cells (e.g., fibroblasts) by artificially inducing the expression of certain genes. In some embodiments, iPSCs may be obtained by transfection of certain stem cell-related genes into non-pluripotent cells such as adult fibroblasts. Transfection may be achieved by viral transduction using virus such as retrovirus or lentivirus. In some embodiments, transfection genes may include the transcription factors Oct4, Sox2, Klf4, and c-Myc, even though simultaneous transfection of other genes has the potential to improve induction efficiency. In some embodiments, a lentiviral system may be utilized to transform somatic cells with Oct4, Sox2, Nanog, and Lin28 genes. Genes inducibly expressed in iPSCs include, but are not limited to, Oct-3/4, certain members of the Sox genc family (e.g., Sox1, Sox2, Sox3, and Sox15), certain members of the Klf family (e.g., Klf1, Klf2, Klf4, and Klf5), and certain members of the Myc family (e.g., C-myc, L-myc, and N-myc), Nanog, Lin28, Tert, Fbx 15, ERas, ECAT15-1, ECAT15-2, Tcl1, β-Catenin, ECAT1, Esg1, Dnmt3L, ECAT8, Gdf3, Fth117, Sal14, Rex1, UTF1, Stella, Stat3, Grb2, Prdm 14, Nr5a1, Nr5a2, or E-cadherin, or any combination thereof. Various reagents for the preparation of iPSCs are already commercially available such as reprogramming vectors, expression cassettes, medium, and the like, and even commercially available iPSCs. The hiPSC refers to iPSC induced from human cells. In some embodiments, the used hiPSC is prepared according to a method (e.g., using the reprogramming factor combinations OCT4, SOX2, E6, and E7) described in the Chinese patent publication CN113462638A, which is hereby incorporated herein by reference to its entirety.

iPSC cells may be derived from any species. iPSC cells have been successfully generated using mouse and human cells. In addition, iPSC cells have been successfully generated using embryonic, fetal, neonatal, and adult tissues. Thus, donor cells from any species may be readily applied to generate iPSC cells, and iPSC cells may be generated from any species, including, but not limited to, humans, non-human primates, rodents (mice, rats), hoofed animals (cows, sheep, etc.), dogs (domestic and wild dogs), felines (domestic and wild felines such as lions, tigers, cheetahs), rabbits, hamsters, goats, elephants, pandas (including giant pandas), pigs, raccoons, horses, zebras, marine mammals (dolphins, whales, etc.), etc.

As used herein, "embryoid body (EB)" refers to an embryoid body or aggregate that is a homogeneous or heterogeneous cell cluster containing differentiated cells, partially differentiated cells, and/or suspension-cultured pluripotent stem cells. In order to generalize some inherent cues of differentiation in vivo, this disclosure uses three-dimensional EBs as an intermediate step. At the onset of cell aggregation, differentiation may be initiated and cells may start to reproduce embryonic development to a limited extent. Although it is unable to form trophoblastic ectodermal tissues, virtually every other type of cell present in an organism may develop. The present disclosure may further promote differentiation of hematopoietic progenitor cells after the formation of the EBs.

As used herein, "mesodermal cell" refers to a cell layer between the ectoderm and the endoderm at the late gastrula stage during the embryonic development of triploblastic animals. Mesodermal cells may develop into the dermis, muscles, bones, and other connective tissues and circulatory system of the body, including the heart, blood vessels, bone marrow, lymph nodes, and lymphatic vessels; the terminal body cavity, the serosa and mesentery of viscera, and connective tissues, blood vessels, and smooth muscles in the viscera; and the kidneys, ureters, gonads (excluding germ cells), germinal tubes, and cortical portions of adrenal glands, etc. As used herein, mesodermal cells refer to cells having mesodermal cell markers (e.g., Braychury) produced by inducing a culture of pluripotent stem cells (iPSCs) in mesoderm induction medium. Accordingly, the process of inducing a culture of iPSC into mesoderm cells is called "mesoderm induction". Methods for generating mesodermal cells by inducing pluripotent stem cells (iPSCs) are known in the art, for example, there are commercially available mesoderm induction medium such as STEMdiff™ mesoderm induction medium. In addition, the Chinese patent publication CN 111321110 A discloses a method for generating mesodermal cells by inducing iPSCs, and the Chinese patent publication CN 106867961A discloses culture media and methods for the induced generation of mesoderm cells, and the Chinese patent publication CN106867961A discloses the medium and method for producing mesoderm cells by inducing iPSC, the contents of each of which are hereby incorporated herein by reference to its entirety.

As used herein, "hematopoietic endothelial cell" refers to cells capable of differentiating to produce hematopoictic cell type or endothelial cell type, which may express PECAM-1, VE-Cadherin, and/or Endoglin (e.g., PECAM1+VE-Cad+Endoglin+Hematopoietic PVE-HE) and be optionally derived from pluripotent stem cells. These cells may be described based on a number of structural and functional properties, including, but not limited to, expression (RNA or protein) or lack of expression (RNA or protein) of one or more markers. Hematopoietic endothelial cells are characterized by the expression of marker CD34 and the non-expression of CD235a. For example, at least about 50%, at least about 60%, or at least about 70%.

As used herein, "monocyte" refers to a cell that is differentiated from a hematopoietic stem cell in the bone marrow and develops in the bone marrow. Monocytes may further differentiate into mature macrophages and dendritic cells. Monocytes are characterized by pronounced deformation movement and have the ability to phagocytose and remove injured and senescent cells and their debris. In addition, monocytes participate in the immune response by transferring antigenic determinants carried by phagocytosis of antigens to lymphocytes and further inducing a specific immune response in lymphocytes. Monocytes also have the ability to recognize and kill tumor cells. In this disclosure, monocytes are obtained by inducing pluripotent stem cells to differentiate under specific conditions, the function of which is not affected.

As used herein, the term "macrophage" usually refers to a myeloid immune cell obtained from development of monocyte penetrating a blood vessel, which is widely distributed in the organs of the body tissues. The main physiological roles of macrophages in normal tissues include: mediating specific immune responses by processing and presenting antigens; devouring and degrading necrotic cells, debris, and foreign substances in the form of either fixed or free cells, and then participating in non-specific responses within the organism; and activating lymphocytes or other immune cells by secreting inflammatory factors, and further coordinating the inflammatory process.

As used herein, "LNCaP cells" refers to a human prostate cancer cell line (PC3 cells) initially isolated from a metastatic lesion of human prostate adenocarcinoma. Unlike PC3 cells, the growth of LNCaP cells is androgen-dependent.

As used herein, "treating and/or preventing" means preventing, reversing, palliating, or inhibiting the disorder or condition to which the term applies, or the progression of one or more symptoms of such disorder or condition. Treating a disease or condition includes ameliorating at least one symptom of a particular disease or condition, even if the basic pathophysiology is not affected. In some embodiments, "treating and/or preventing blood system diseases" includes one or more of the following: (1) preventing the occurrence of the blood system diseases; (2) inhibiting the progression of the blood system diseases; (3) curing the blood system diseases; (4) alleviating the symptoms associated with the patient with the blood system diseases; (5) reducing the severity of the blood system diseases; (6) preventing the recurrence of the blood system diseases.

Embodiments of the present disclosure provide a medium combination and a method for inducing iPSC differentiation to obtain macrophages and use thereof. By optimizing the culture method and culture conditions, the macrophage yield is increased, and the culture cost is reduced, about 188,000 macrophages may be obtained from 1 iPSC, and the obtained macrophages have good phagocytic function.

Embodiments of the present disclosure provide a medium combination for inducing iPSC differentiation to obtain macrophages, comprising a first stage medium, a second stage medium, a third stage medium, a fourth stage medium, a fifth stage medium, and a sixth stage medium. The iPSC differentiation is sequentially cultured from the first stage to the sixth stage over time, with the first stage medium to the sixth stage medium sequentially.

In some embodiments, the first stage medium is an E8 complete medium containing a ROCK pathway inhibitor and polyvinyl alcohol, the second stage medium is an E8 complete medium containing a GSK-3β inhibitor, the third stage medium comprises M1 medium and M2 medium, the fourth stage medium is M3 medium, the fifth stage medium is M4 medium, and the sixth stage medium is M5 medium.

In some embodiments, the M1 medium includes a stempro-34 complete medium, DMEM/F12, L-glutamine, ascorbic acid, Insulin-Transferrin-Selenium-Ethanolamine, BMP4, VEGF, and bFGF, and M2 medium includes M1 medium and inhibitors of TGF-β type I receptors ALK5, ALK4, and ALK7.

In some embodiments, the M3 medium comprises X-VIVOTM 15, L-glutamine, ascorbic acid, Insulin-Transferrin-Selenium-Ethanolamine, NEAA, β-mercaptoethanol, BMP4, VEGF, bFGF, SCF, IL-3, and M-CSF.

In some embodiments, the M4 medium comprises X-VIVOTM 15, L-glutamine, ascorbic acid, Insulin-Transferrin-Selenium-Ethanolamine, NEAA, β-mercaptoethanol, IL-3, and M-CSF.

In some embodiments, the M5 medium comprises X-VIVOTM 15, L-glutamine, ascorbic acid, Insulin-Transferrin-Selenium-Ethanolamine, NEAA, β-mercaptoethanol, and M-CSF.

In some embodiments of the present disclosure, by adopting an optimized medium combination, the macrophage yield can be increased and the culture cost can be reduced, about 188,000 macrophages can be obtained from 1 iPSC, and the obtained macrophages have good phagocytosis function.

In some embodiments, the ROCK pathway inhibitor in the first stage medium is selected from the group consisting of Y-27632, Thiazovivin, Fasudil (HA-1077) HCl, GSK429286A, RKI-1447, and Azaindole 1. In some embodiments, the ROCK pathway inhibitor is Y-27632.

In some embodiments, the GSK-3β inhibitor in the second stage medium is selected the group consisting of CHIR-99021, SB216763, CHIR-98014, TWS119, Tideglusib, and SB415286. In some embodiments, the GSK-3β inhibitor is CHIR-99021.

In some embodiments, the inhibitors of TGF-β type I receptors ALK5, ALK4, and ALK7 in the M2 medium are selected from the group consisting of SB431542, Galunisertib (LY2157299), LY2109761, SB525334, SB505124, and GW788388.

In some embodiments of the present disclosure, by employing the preferred ROCK pathway inhibitor, the preferred GSK-3β inhibitor, and the preferred inhibitors of the TGF-β type I receptors ALK5, ALK4, and ALK7, the macrophage yield can be increased and the culture cost can be reduced.

In some embodiments, the concentration of Y-27632 in the first stage medium is within a range of 0.5-20 μM. In some embodiments, the concentration of Y-27632 in the first stage medium is 10 μM and the concentration of polyvinyl alcohol in the first stage medium is 4 mg/mL.

In some embodiments, the concentration of CHIR-99021 in the second stage medium is within a range of 1-10 μM. In some embodiments, the concentration of CHIR-99021 in the second stage medium is 10 μM.

In some embodiments, in the third stage medium, the M1 medium comprises 50 wt % stempro-34 complete culture, 50 wt % DMEM/F12, 1 wt % L-glutamine, 50 μg/mL ascorbic acid, 1× Insulin-Transferrin-Selenium-Ethanolamine, 50 μg/mL BMP4, 50 μg/mL VEGF, and 50 μg/mL bFGF. In some embodiments, the M2 medium comprises M1 medium and 1-9 μM SB431542. In some embodiments, the concentration of the SB431542 in the M2 medium is 6 μM.

In some embodiments, in the fourth stage medium, the M3 medium comprises X-VIVOTM 15, 1 wt % L-glutamine, 50 μg/mL ascorbic acid, 1× Insulin-Transferrin-Selenium-Ethanolamine, 1×NEAA, 55 μM β-mercaptoethanol, 50 μg/mL BMP4, 50 g/mL VEGF, 50 μg/mL bFGF, 50 μg/mL SCF, 25 μg/mL IL-3, and 100 μg/mL M-CSF.

In some embodiments, in the fifth stage medium, the M4 medium comprises X-VIVOTM 15, 1 wt % L-glutamine, 50 μg/mL ascorbic acid, 1× Insulin-Transferrin-Selenium-Ethanolamine, 1×NEAA, 55 μM β-mercaptoethanol, 25 μg/mL IL-3, and 100 μg/mL M-CSF.

In some embodiments, in the sixth stage medium, the M5 medium comprises X-VIVOTM 15, 1 wt % L-glutamine, 50 μg/mL ascorbic acid, 1× Insulin-Transferrin-Selenium-Ethanolamine, 1×NEAA, 55 μM β-mercaptoethanol, and 100 μg/mL M-CSF.

In some embodiments of the present disclosure, the use of the above first stage medium to sixth stage medium can optimally increase macrophage yield and maximize the reduction of culture cost.

In some embodiments, the medium combination for inducing iPSC differentiation to obtain macrophages further comprises a seventh stage medium, and the seventh stage medium comprises an M6 medium or an M7 medium.

In some embodiments, the M6 medium comprises X-VIVOTM 15, 1 wt % L-glutamine, 50 μg/mL ascorbic acid, 1× Insulin-Transferrin-Selenium-Ethanolamine, 1×NEAA, 55 μM β-mercaptoethanol, 20 μg/mL IFN-γ, and 50 μg/mL LPS.

In some embodiments, the M7 medium comprises X-VIVOTM 15, 1 wt % L-glutamine, 50 μg/mL ascorbic acid, 1× Insulin-Transferrin-Selenium-Ethanolamine, 1×NEAA, 55 μM β-mercaptoethanol, 20 g/mL IL-4, and 20 μg/mL IL-13.

In some embodiments of the present disclosure, M0 macrophages can be polarized towards M1 macrophages or M2 macrophages by employing the seventh stage medium.

Embodiments of the present disclosure also provide a kit for inducing iPSC differentiation to obtain macrophages, comprising the first stage medium, the second stage medium, the third stage medium, the fourth stage medium, the fifth stage medium, and the sixth stage medium, or the first stage medium, the second stage medium, the third stage medium, the fourth stage medium, the fifth stage medium, the sixth stage medium, and the seventh stage medium.

In some embodiments of the present disclosure, it is convenient to culture iPSC into macrophages by making kits from the first stage medium, the second stage medium, the third stage medium, the fourth stage medium, the fifth stage medium, and the sixth stage medium, or from the first stage medium, the second stage medium, the third stage medium, the fourth stage medium, the fifth stage medium, the sixth stage medium, and the seventh stage medium.

Embodiments of the present disclosure also provide a method for inducing iPSC differentiation to obtain macrophages by using the medium combination, comprising the following steps.

(a) a first stage, formation of EBs: forming the EBs by suspension culture of the iPSC under a normoxic condition for 1 day using the first stage medium.

(b) a second stage, differentiation of the EBs into mesoderm: forming mesodermal cells by differentiation induction culture of the EBs under an anoxic condition for 1 day using the second stage medium.

(c) a third stage, differentiation of the mesodermal cells into hematopoietic endothelial cells: forming the hematopoietic endothelial cells by induction culture of the mesodermal cells under the anoxic condition for 3 days using the third stage medium.

In some embodiments, induction culture of the mesodermal cells is performed using the M1 medium for the first day of the third stage, and the induction culture of the mesodermal cells is continued to be performed using M2 medium instead of the M1 medium for the last two days of the third stage.

(d) a fourth stage, differentiation of the hematopoietic endothelial cells into myeloid progenitor cells: forming the myeloid progenitor cells by induction culture of the hematopoietic endothelial cells in a cell culture dish coated with matrigel under the normoxic condition for 8 days using the fourth stage medium.

(e) a fifth stage, differentiation of the myeloid progenitor cells into monocytes: forming the monocytes by induction culture of the myeloid progenitor cells under the normoxic condition for 14 days using the fifth stage medium.

In some embodiments, induction culture of the myeloid progenitor cells is performed in the cell culture dish coated with the matrigel for the first 7 days of the fifth stage, and the induction culture of the myeloid progenitor cells is continued to be performed in the cell culture dish without the matrigel for the last 7 days of the fifth stage.

(f) a sixth stage, differentiation of the monocytes into M0 macrophages: obtaining the M0 macrophages by induction culture of the monocytes under the normoxic condition for 7 days using the sixth stage medium.

In some embodiments, the matrigel includes, but is not limited to, Mtrigel, Geltin (CAS No.: 9000-70-8), Lamin521, or Fibronection.

In some embodiments of the present disclosure, by adopting an optimized culture method and culture conditions, the macrophage yield can be increased and the culture cost can be reduced, about 188,000 macrophages can be obtained from 1 iPSC, and the obtained macrophages have good phagocytosis.

In some embodiments, the method of inducing iPSC differentiation to obtain macrophages further comprises: (g) in a seventh stage, differentiating the M0 macrophages into M1 macrophages or M2 macrophages.

In some embodiments, when the M1 macrophages are required to be obtained by polarization, a culture of the M0 macrophages is induced under the normoxic condition for 2 days using M6 medium to obtain the M1 macrophages; or a culture of the M0 macrophages is induced under the normoxic condition using M7 medium to obtain the M2 macrophages, and then a culture of the M2 macrophages is induced under the normoxic condition for 2 days using the M7 medium to obtain the M1 macrophages for 2 days under the normoxic condition to obtain M1 macrophages.

In some embodiments, when the M2 macrophages are required to be obtained by polarization, a culture of the M0 macrophages is induced under the normoxic condition on day 34 and day 35 using the M7 medium to obtain the M2 macrophages.

In some embodiments of the present disclosure, by the optimized culture method and the optimized culture condition as described above, it is possible to polarize M0 macrophages to M1 macrophages or M2 macrophages, and to polarize M2 macrophages to M1 macrophages.

In some embodiments, the normoxic condition in steps (a) and (d)-(g) includes 5% CO2 and 37° C. and the hypoxic condition in steps (b-c) includes 5% $CO_2$, 90% $N_2$, and 37° C.

In some embodiments, in step (c), half-medium change is performed once on day 3, and in steps (d)-(c), half-exchange is performed once every 3 days.

In some embodiments of the present disclosure, it enables optimal conversion of iPSCs into macrophages by the above optimized culture method and culture condition.

Embodiments of the present disclosure further provide a pharmaceutical composition comprising one or more of M0 macrophages, M1 macrophages, and M2 macrophages obtained by the above preparation.

In some embodiments, the pharmaceutical composition further comprises pharmaceutically acceptable carriers and/or excipients. In Remington's Pharmaceutical Sciences (19th ed., 1995), detailed records are provided that these substances are used as needed to aid in the stability of the formulation or to contribute to enhancing the activity or bioefficacy or to produce an acceptable taste or odor in the case of oral administration, and the preparations used in such pharmaceutical compositions may be in the form of their original compounds, or optionally in the form of pharmaceutically acceptable salts thereof. Preferably, the pharmaceutically acceptable carriers and/or excipients comprise pharmaceutically acceptable carriers, diluents, fillers, binding agents, and other excipients, depending on the mode of administration and the form of designed dosage.

In some embodiments, the pharmaceutical composition is in any pharmaceutically acceptable dosage form, including at least one of a tablet, a capsule, an injection, a granule, a suspension, or a solution.

In some embodiments, the actual dosage of the active ingredient (one or more of M0 macrophages, M1 macrophages, and M2 macrophages) in the pharmaceutical composition may be determined based on a variety of relevant factors, including the severity of the disease to be treated, the route of administration, the patient's age, gender, and body weight. The above dosage should therefore not limit the protection scope of this disclosure in any way.

In some embodiments, a suitable administered dosage of a pharmaceutical composition may be prescribed based on factors such as the method of formulation, the mode of administration, the patient's age, weight, gender, disease state, diet, time of administration, route of administration, rate of excretion, and responsiveness, and a skilled physician can usually easily determine the prescription and the effective dosage for the desired treatment.

Embodiments of the present disclosure further provide a use of the pharmaceutical composition, and a use of the pharmaceutical composition in the preparation of drugs for the treatment and/or prevention of blood system diseases and/or autoimmune diseases and/or solid tumors.

In some embodiments, the blood system diseases include chronic granulocytic leukemia, acute myeloid leukemia, acute lymphoblastic leukemia, non-Hodgkin's lymphoma, Hodgkin's lymphoma, multiple myeloma, myelodysplastic syndrome, aplastic disorders, Fanconi anemia, thalassemia, sickle cell anemia, myelofibrosis, severe paroxysmal sleep hemoglobinuria, and megakaryocytic thrombocytopenia.

In some embodiments, the autoimmune diseases include refractory rheumatoid arthritis, systemic lupus erythematosus, multiple sclerosis, juvenile idiopathic arthritis, systemic sclerosis, Wegener's granulomatosis, antiphospholipid antibody syndrome, severe critical myasthenia gravis, Crohn's disease, diabetes mellitus type 1, and severe combined immunodeficiency.

In some embodiments, the solid tumors include breast cancer, ovarian cancer, testicular cancer, neuroblastoma, small cell lung cancer, nasopharyngeal carcinoma, retroperitoneal yolk cystic tumors, Ewing's sarcoma, primitive neural ectodermal tumors, nephroblastomas, hepatocellular carcinomas, malignant schwannoma, and retinoblastoma.

The technical solutions of the present disclosure are described in further detail below in connection with specific examples. It should be understood that the following examples are only exemplary for illustrating and explaining the present disclosure, and should not be construed as a limitation on the scope of protection of the present disclosure. Any technology realized based on the foregoing contents of this disclosure is covered by the scope of protection intended by this disclosure.

EXAMPLES

The experimental materials involved in the examples of this disclosure were shown in Table 1.

TABLE 1

Experimental materials

| Name | Manufacturer | Product code |
|---|---|---|
| Matrigel | Corning | 354277 |
| X-VIVOTM 15 | Lonza | 04-418Q |
| NEAA (100X) | Thermo | 11140-050 |
| Beta-Mercaptoethnol(1000X) | Thermo | 21985-023 |
| GlutaMAX-I (100X) | Gibco | 35050061 |
| Insulin-Transferrin-Selenium-X | Gibco | 51500056 |
| L-ascorbic acid | sigma | A92902 |
| BMP4 | Peprotech | 120-05ET |
| Animal-Free Recombinant Human FGF-basic (154 a.a.) | peprotech | AF-100-18B |

TABLE 1-continued

Experimental materials

| Name | Manufacturer | Product code |
|---|---|---|
| Animal-Free Recombinant Human VEGF165 | peprotech | AF-100-20 |
| CHIR99021 | StemCell Technologies | 72054 |
| SB431542 | abcam | ab120163 |
| 0.25% Trypsin-EDTA(1X) | Thermo | 25200072 |
| E8 Basal Medium | STEMCELL | 05991 |
| E8 25X Supplement | STEMCELL | 05992 |
| Recombinant Human TPO | peprotech | 300-18-10 |
| Recombinant Human SCF | peprotech | 300-07 |
| Animal-Free Recombinant Human Flt3-Ligand | peprotech | AF-300-19 |
| Animal-Free Recombinant Human IL-3 | peprotech | AF-200-03 |
| Recombinant Human M-CSF | Biolegend | 574808 |

Example 1 Induction of iPSC Differentiation to Obtain Macrophages

1. Method for Inducing iPSC Differentiation to Obtain Macrophages

This method for inducing iPSC differentiation to obtain macrophages comprised the following steps.

S1, Formation of EBs (1) The iPSC was prepared by Beijing Chennuo Medical Science and Technology Co., Ltd. by the method described in Chinese patent application CN202110733296.8, or by the method described in Chinese patent application CN201910110768.7, or by a method known in the art or a commercialized kit. After iPSC confluence reached 70% (the cell morphology is shown in the cell morphology image of FIG. 1), the supernatant was removed, cells were washed twice by adding pre-warmed Dulbecco's Phosphate Buffered Saline (DPBS), then the pre-warmed Tryple (recombinant enzyme tryple, Tryple Express) was added to digest the cells into a single-cell state, and after terminating digestion and centrifugation, the supernatant was removed, and cells were resuspended in the complete medium containing E8 including 10 μM Y-27632 and 4 mg/mL polyvinyl alcohol (PVA) for cell counting.

(2) The cell density was adjusted to $1.0 \times 10^4$-$2 \times 10^4$/mL, the cells were inoculated into low adsorption six-well plates with 3 mL of medium per well, i.e., 100,000-500,000 cells per well (preferably 300,000 cells per well), and the cells were incubated in a constant temperature incubator with 5% $CO_2$ at 37° C. for 24 h to obtain EBs, which was recorded as Day-1.

In some embodiments, the ROCK pathway inhibitor may also be Thiazovivin, Fasudil (HA-1077) HCl, GSK429286A, RKI-1447, or Azaindole 1.

S2, Induction of EBs Differentiation Into Mesoderm

Figure 2:
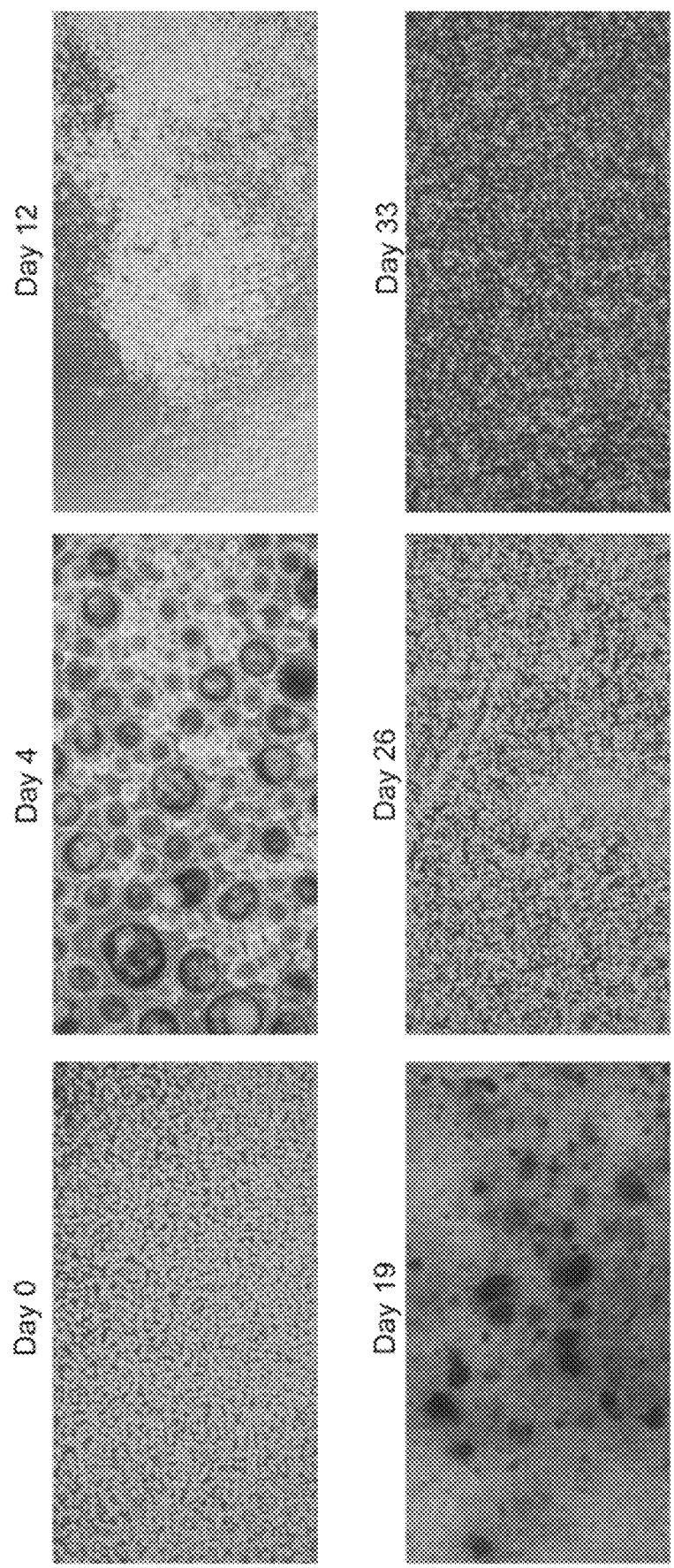
FIG. 2 is a cell morphology image of cells on day 0, day 4, day 12, day 19, day 26, and day 33 during the differentiation process under a 4× optical microscope according to some embodiments of the present disclosure.

The EBs were transferred to a centrifuge tube and centrifuged at 20 g for 2 min to remove the supernatant, and E8 complete medium containing 10 μM GSK-3β inhibitor CHIR-99021 was added to initiate mesodermal differentiation, which was recorded as Day 0, and the cells were incubated in a constant temperature incubator with 5% $CO_2$ and 90% $N_2$, at 37° C. for 24 h to obtain mesodermal cells (the cell morphology is shown in the cell morphology image on day 0 of FIG. 2);

In some embodiments, the GSK-3β inhibitor may also be SB216763, CHIR-98014, TWS119, Tideglusib, or SB415286. The differentiation induction basic medium may also be E8 complete medium (TeSR™-E8™, purchased from Beijing Nuowei Bio), StemPro-34 (StemPro®-34

SFM, purchased from Pfeiffer Bio), Stemline® II (purchased from Beijing Nuowei Bio), or STEMdiff™ APEL™2 Medium (purchased from Beijing Nuowei Bio).

S3, Induction of Mesodermal Cell Differentiation to Hematopoietic Endothelial Cells (1) On day 1, the E8 complete medium was replaced with M1 medium, the M1 medium included 50% tempo-34 complete medium, 50% DMEM/F12 (purchased from Shangen Bio), 1% L-glutamine, 50 μg/mL ascorbic acid, 1× Insulin-Transferrin-Selenium-Ethanolamine (ITSE, purchased from Yanhui), 50 μg/mL BMP4 (protein number: P12644 (S293-R408)), 50 μg/mL Vascular Endothelial Growth Factor (VEGF), and 50 μg/mL Basic Fibroblast Growth Factor (bFGF), and the obtained EBs on Day 0 were resuspended in M1 medium and incubated in the constant temperature incubator with 5% $CO_2$ and 90% $N_2$ at 37° C. for 24 h.

(2) On day 2, the M1 medium was replaced with the M2 medium, the M2 medium also included 6 μM SB431542 inhibitor (inhibitor of TGF-β type I receptors ALK5, ALK4, and ALK7) on the basis of M1 medium, and 3 mL M2 medium was added to each well, and the obtained EBs on day 1 were resuspended in the M2 medium and incubated in a constant temperature incubator with 5% $CO_2$ and 90% $N_2$ at 37° C. for 24 h.

(3) On day 3, the half-medium change was performed, the culture plates were stood for 1 min, 1.5 mL supernatant was removed, and 1.5 mL M2 medium was added to obtain hematopoietic endothelial cells.

In some embodiments, the inhibitors of the TGF-β type I receptors ALK5, ALK4, and ALK7 may also be 1-12 μM Galunisertib (LY2157299), 1-12 μM LY2109761, 1-10 μM SB525334, 1-10 μM SB505124, or 1-10 μM GW788388.

S4, Induction of Hematopoietic Endothelial Cells Differentiation to Myeloid Progenitor Cells On day 4 of differentiation, the EBs were transferred to cell culture dishes coated with matrigel, and the medium was replaced with M3 medium, the M3 medium included X-VIVOTM 15, 1% L-glutamine, 50 μg/mL ascorbic acid, 1× Insulin-Transferrin-Selenium-Ethanolamine, 1×NEAA, 55 μM β-mercaptoethanol, 50 μg/mL BMP4, 50 g/mL VEGF, 50 μg/mL bFGF, 50 μg/mL SCF, 25 μg/mL IL-3, and 100 μg/mL M-CSF, and the EBs were incubated in a constant temperature incubator with 5% $CO_2$ at 37° C. until Day 12, during which the half-medium change was performed once every 3 days, to obtain myeloid progenitor cells. Cell morphology of cells on Day 4 and Day 12 during the differentiation process under the 4× optical microscope is shown in FIG. 2. On day 4, the suspended cells were collected for flow cytometry to detect CD34 and CD235a expression (shown in FIG. 4). On day 12, the suspended cells were collected for flow cytometry to detect CD45, CD14, and CD11b expression (as shown in FIGS. 5A and 5B).

In some embodiments, the matrigel may also be Mtrigel, Geltin (CAS No.: 9000-70-8), Lamin521, or Fibronection.

Figure 6A:
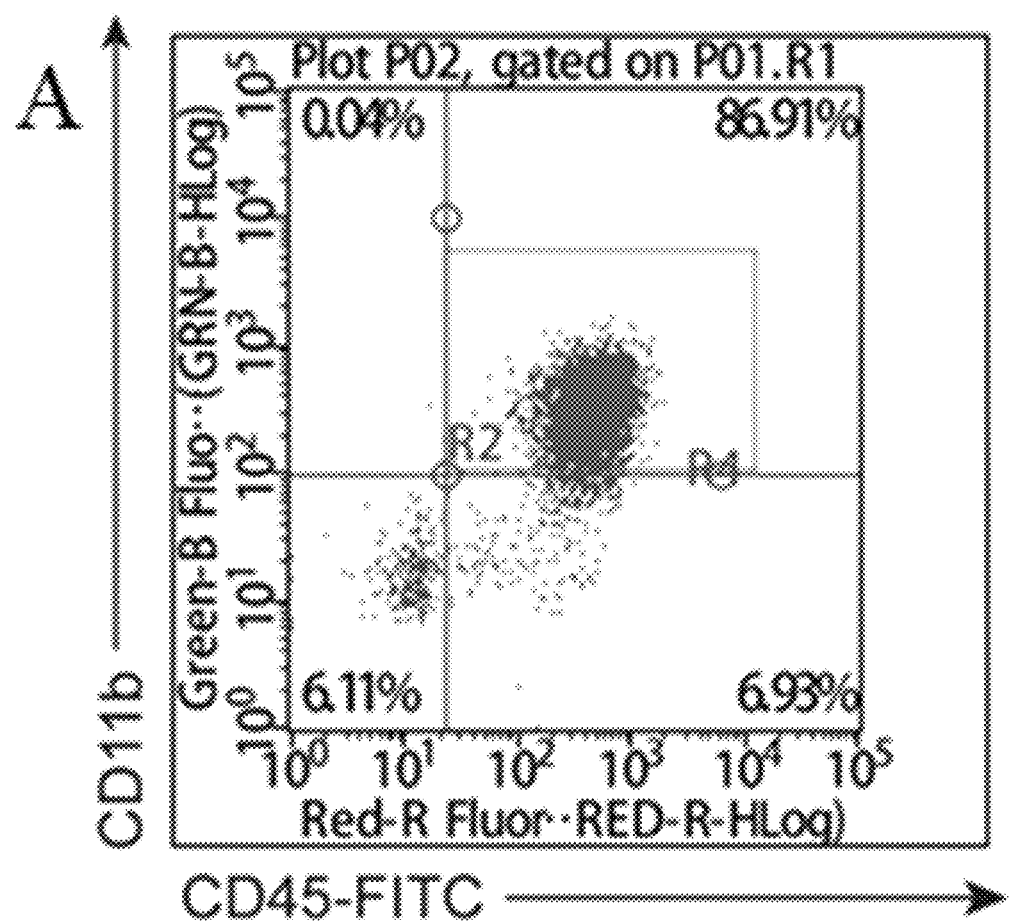
FIG. 6A is a detection diagram of the expression of CD45 and CD11b on day 19 of differentiation according to some embodiments of the present disclosure.
Figure 6B:
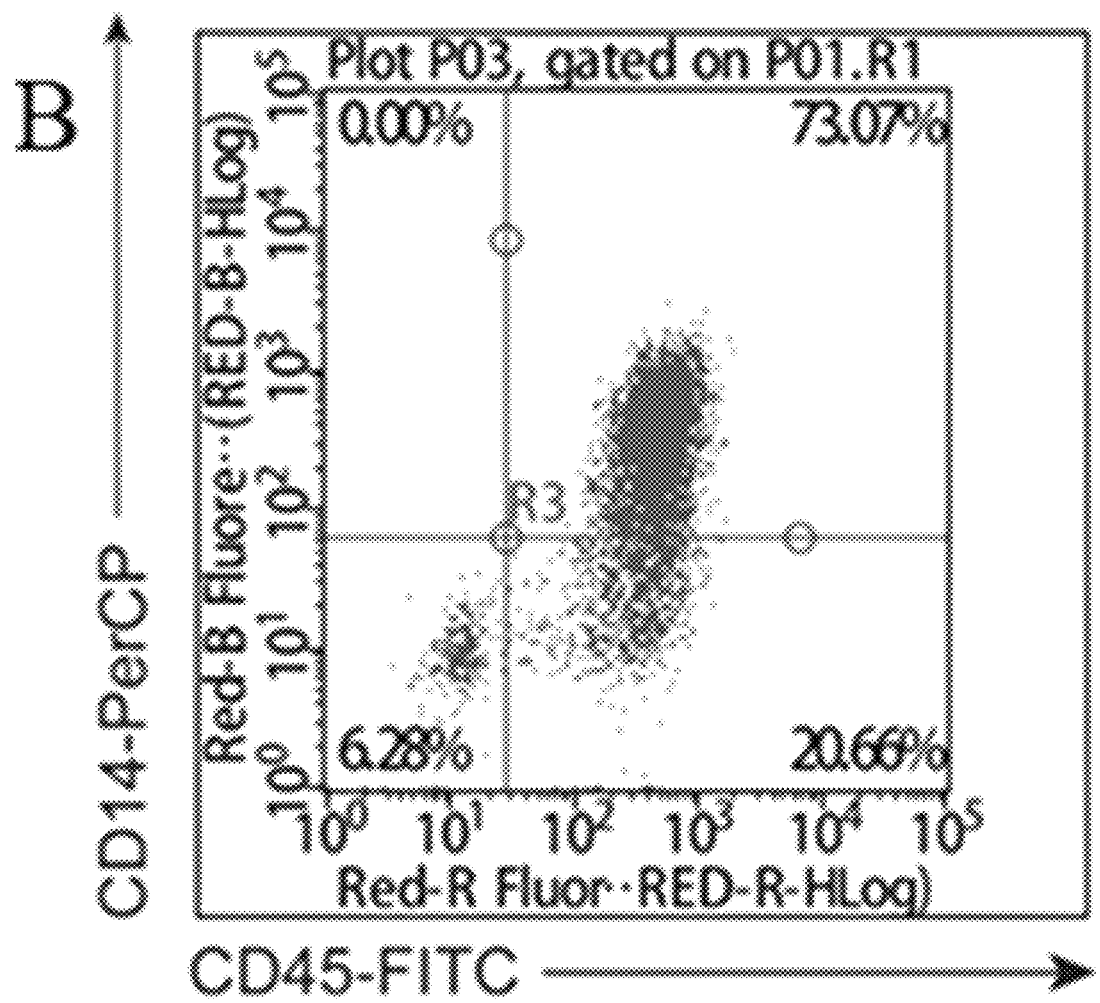
FIG. 6B is a detection diagram of the expression of CD45 and CD14 on day 19 of differentiation according to some embodiments of the present disclosure.

S5, Induction of Myeloid Progenitor Cells Differentiation to Monocytes (1) On day 13 of differentiation, the medium was replaced with M4 medium, the M4 medium included X-VIVOTM 15, 1% L-glutamine, 50 μg/mL ascorbic acid, 1×Insulin-Transferrin-Selenium-Ethanolamine, 1×NEAA, 55 μM β-mercaptoethanol, 25 μg/mL IL-3, 100 μg/mL M-CSF, and the cells were incubated in a constant temperature incubator with 5% $CO_2$ at 37° C. until Day 19, during which the half-medium change was performed once every 3 days;

On day 19, the suspended cells were collected for flow cytometry to detect CD45, CD14, and CD11b expression (shown in FIGS. 6A and 6B).

(2) On day 20 of differentiation, the suspended cells were transferred to a culture dish without matrigel, the cell density was adjusted to $1.0×10^5$/cm$^2$, and the cells were incubated in a constant temperature incubator with 5% $CO_2$ at 37° C. until Day 26, during which the half-medium change was performed once every 3 days, to obtain the mononuclear cells. Cell morphology of cells on Day 19 and Day 26 during the differentiation process under the 4× optical microscope was shown in FIG. 2. On day 26, the suspended cells were collected for flow cytometry to detect CD45, CD14, and CD11b expression (shown in FIGS. 7a and 7B). Detection was performed on cells on Day 26 of differentiation using Giemsa staining, as shown in FIG. 8.

S6, Induction of Monocytes Differentiation Into M0 Macrophages

Figure 9A:
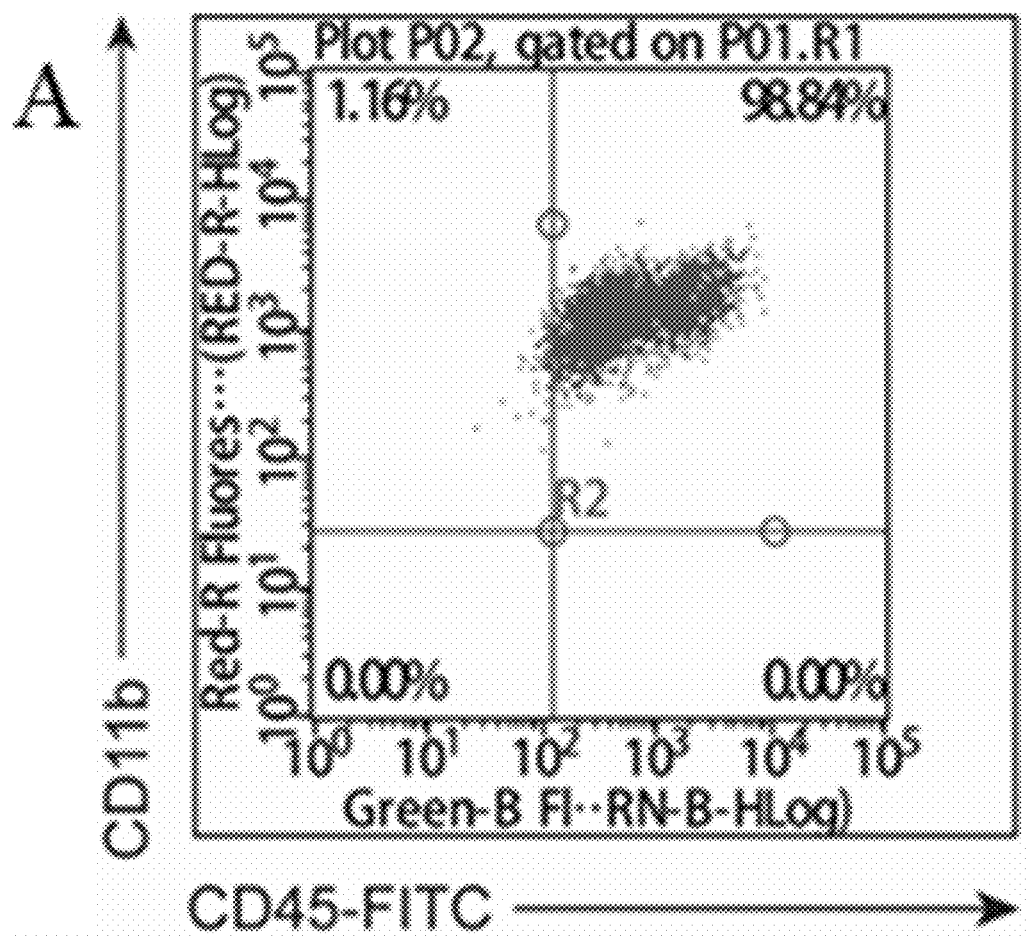
FIG. 9A is a detection diagram of the expression of CD45 and CD11b on day 33 of differentiation according to some embodiments of the present disclosure.
Figure 9B:
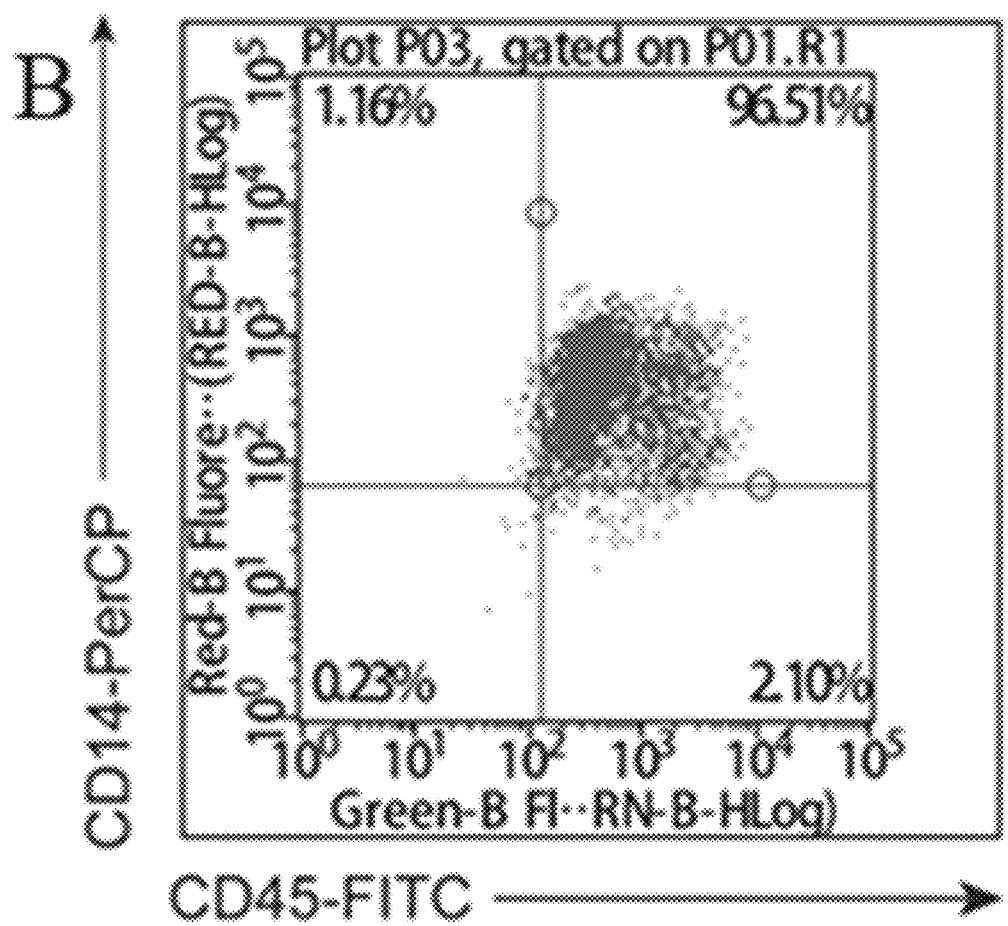
FIG. 9B is a detection diagram of the expression of CD45 and CD14 on day 33 of differentiation according to some embodiments of the present disclosure.
Figure 10A:
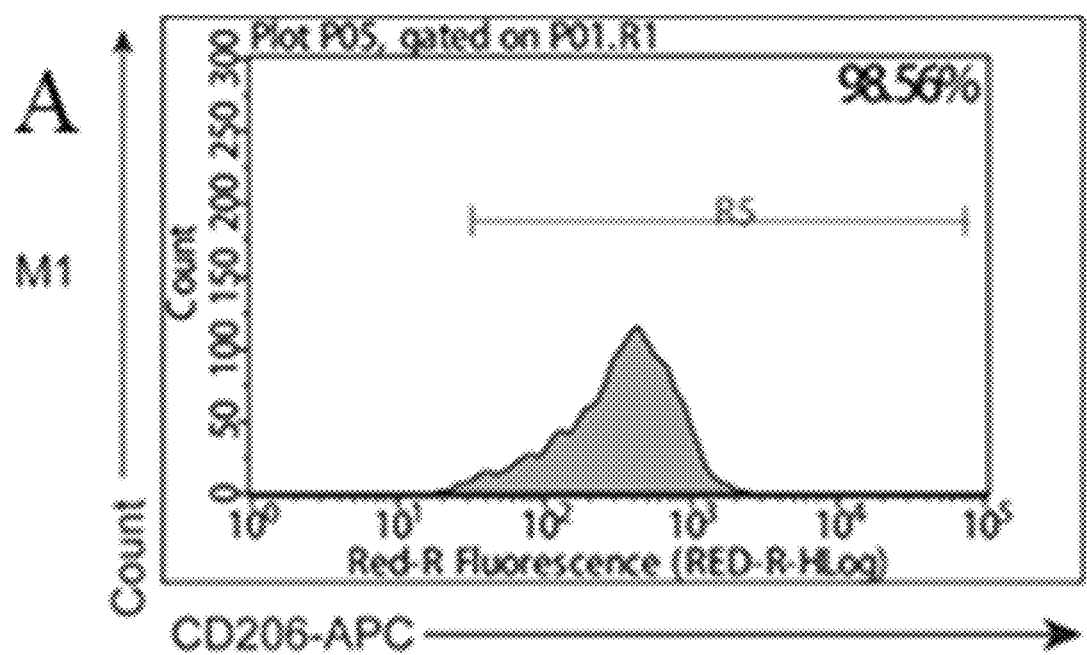
FIG. 10A is a detection diagram of the expression of CD206 of M1 macrophages according to some embodiments of the present disclosure.
Figure 10B:
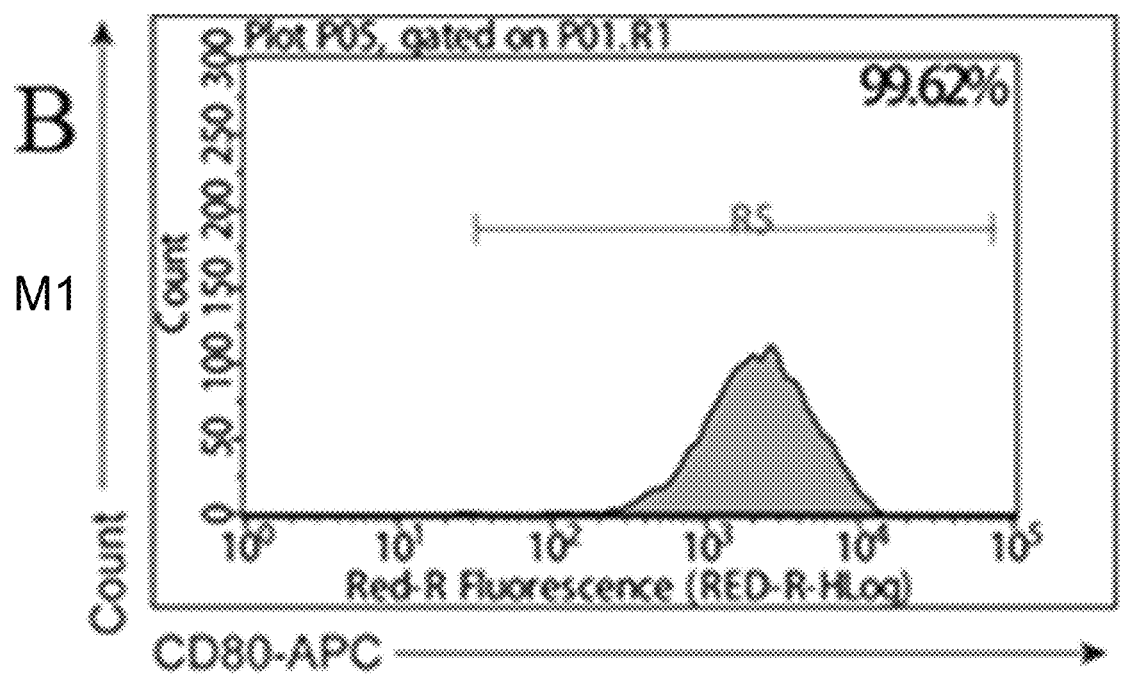
FIG. 10B is a detection diagram of the expression of CD80 of M1 macrophages according to some embodiments of the present disclosure.
Figure 10C:
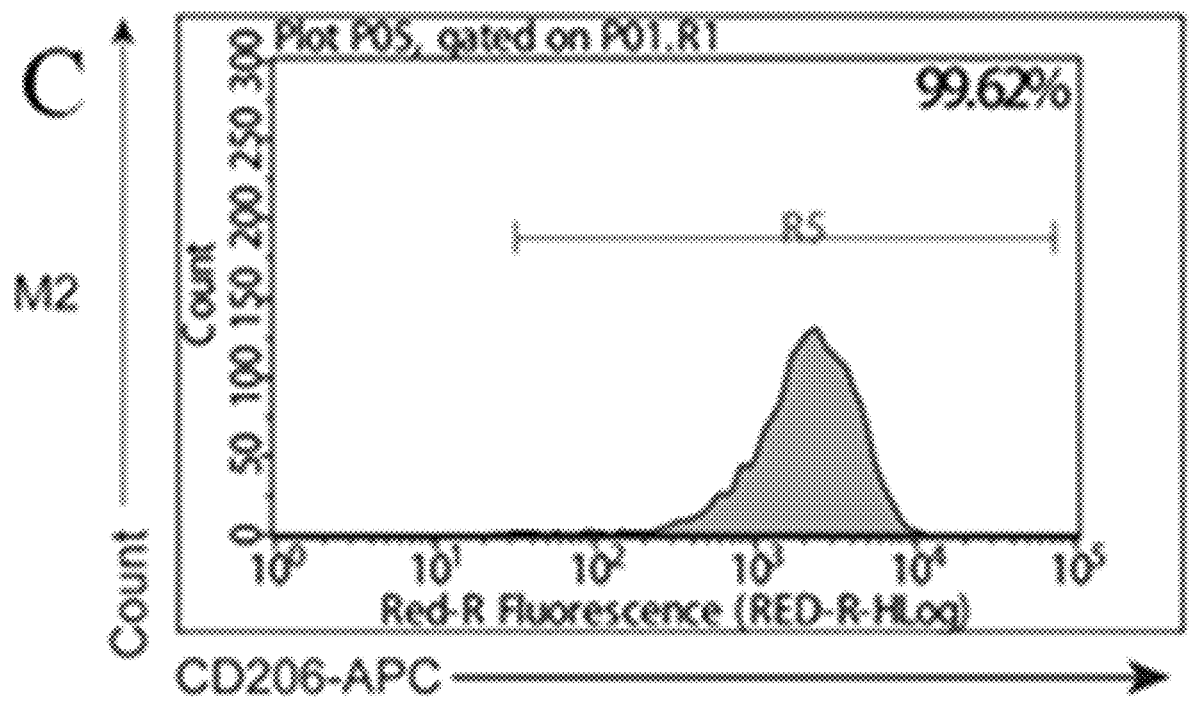
FIG. 10C is a detection diagram of the expression of CD206 of M2 macrophages according to some embodiments of the present disclosure.
Figure 10D:
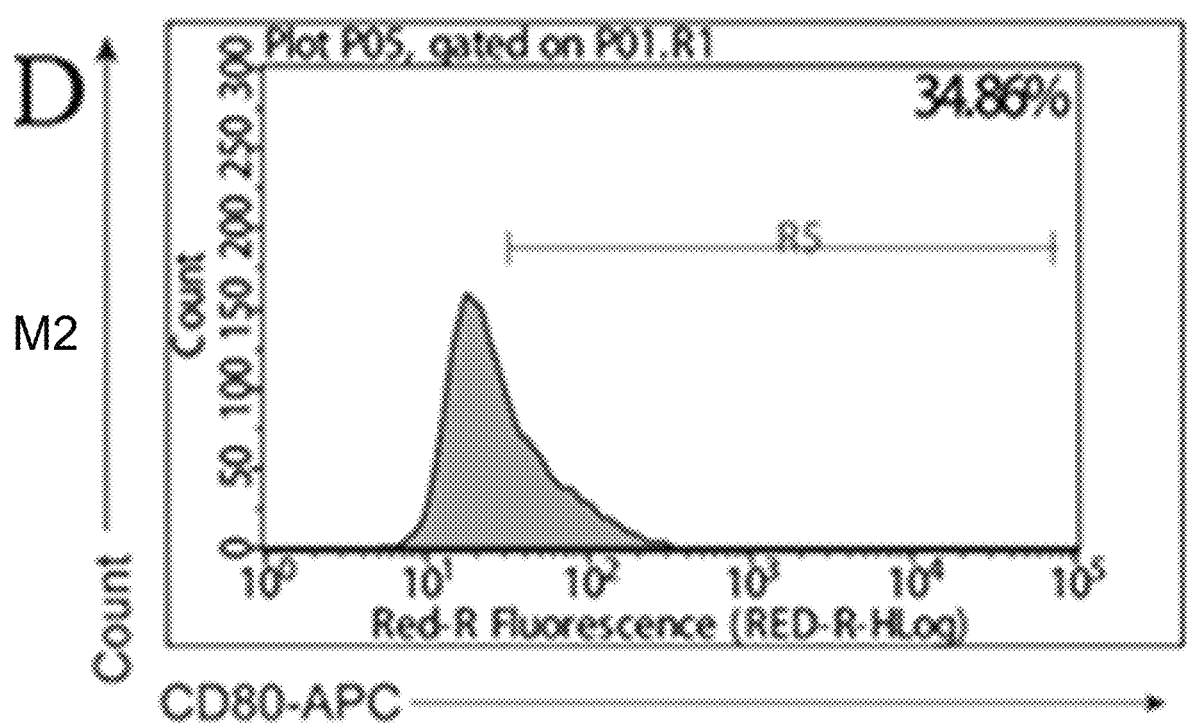
FIG. 10D is a detection diagram of the expression of CD80 of polarized M2 macrophages according to some embodiments of the present disclosure.

On day 27 of differentiation, the cell density was adjusted to $3.0×10^4$/cm$^2$, and the medium was replaced with M5 medium, the M5 medium included X-VIVOTM 15, 1% L-glutamine, 50 μg/mL ascorbic acid, 1× Insulin-Transferrin-Selenium-Ethanolamine, 1×NEAA, 55 μM β-mercaptoethanol, 100 μg/mL M-CSF, and the cells were incubated in the constant temperature incubator with 5% $CO_2$ at 37° C. until Day 33, during which the half-medium change was performed once every 3 days, to obtain the M0 macrophages. Cell morphology of cells on day 33 during the differentiation process under the 4× optical microscope is shown FIG. 2. On day 33, the suspended cells were collected for flow cytometry to detect CD45, CD14, and CD11b expression (as shown in FIGS. 9A and 9B).

S7, Induction of Polarization of M0 Macrophage Into M1 Macrophages and M2 Macrophages (1) Polarization was performed on the obtained M0 macrophages on day 34 of differentiation. If M1 macrophages are required to be obtained by polarization, the medium was replaced with M6 medium, the M6 medium included X-VIVOTM 15, 1% L-glutamine, 50 μg/mL ascorbic acid, 1× Insulin-Transferrin-Selenium-Ethanolamine, 1×NEAA, 55 μM β-mercaptoethanol, 20 μg/mL IFN-γ, and 50 μg/mL lipopolysaccharide (LPS, Sigma-Aldrich), and the cells were incubated in the constant temperature incubator with 5% $CO_2$ at 37° C. for 2 days to obtain M1 macrophages.

(2) If M2 macrophages are required to be obtained by polarization, the medium was replaced with M7 medium, the M7 medium included X-VIVOTM 15, 1% L-glutamine, 50 μg/mL ascorbic acid, 1× Insulin-Transferrin-Selenium-Ethanolamine, 1×NEAA, 55 μM β-mercaptoethanol, 20 μg/mL Interleukin (IL-4, purchased from Saiye Biotechnology Co., Ltd.), and 20 μg/mL Recombinant Human Interleukin 13 (IL-13, purchased from Eimage Technology), and the cells were incubated in the constant temperature incubator with 5% $CO_2$ at 37° C. for 2 days to obtain M2 macrophages. Suspended cells of M1 macrophages and M2 macrophages were collected for flow cytometry to detect CD206 and CD80 expression (shown in FIGS. 10A-10D).

(3) Induction of Polarization of M2 Macrophages Into M1 Macrophages

Figure 11:
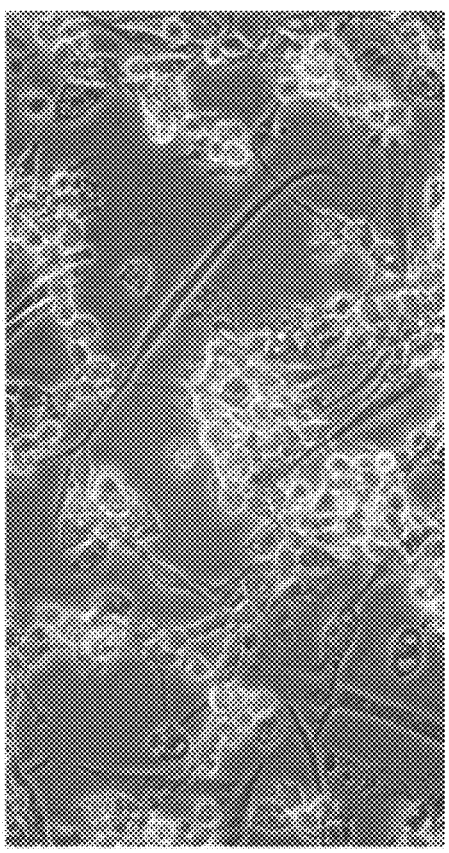
FIG. 11 is a cell morphology image illustrating the transformation of M2 macrophages to M1 macrophages according to some embodiments of the present disclosure.
Figure 11:
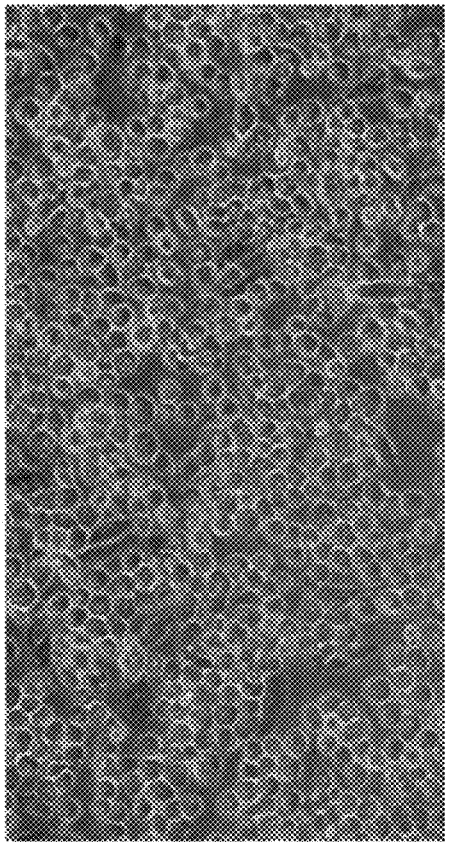
Figure 12A:
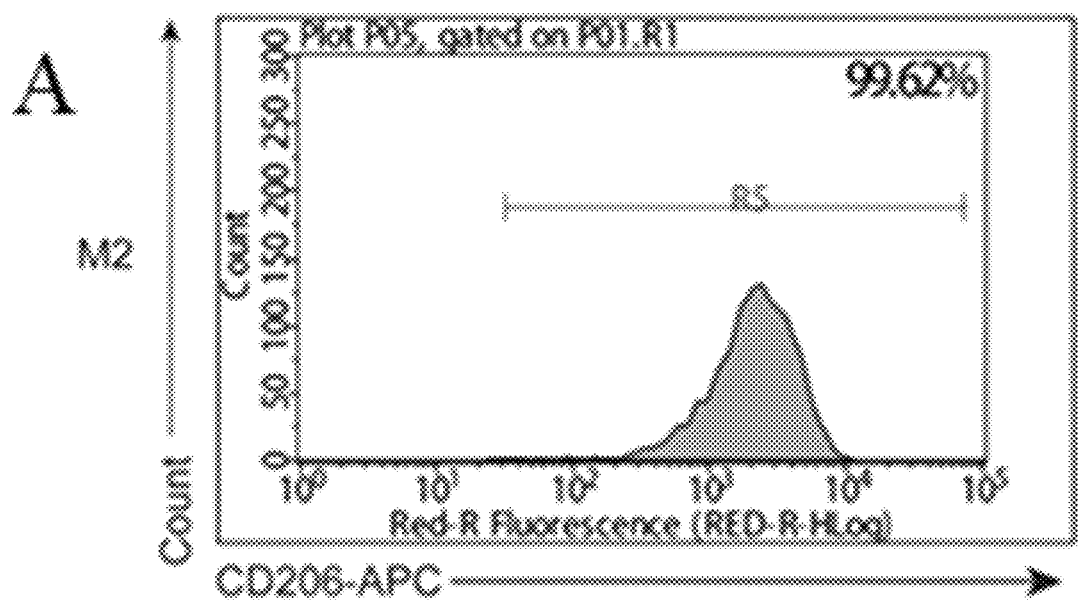
FIG. 12A is a diagram illustrating flow cytometry analysis of the expression of CD206 of M2 macrophages according to some embodiments of the present disclosure.
Figure 12B:
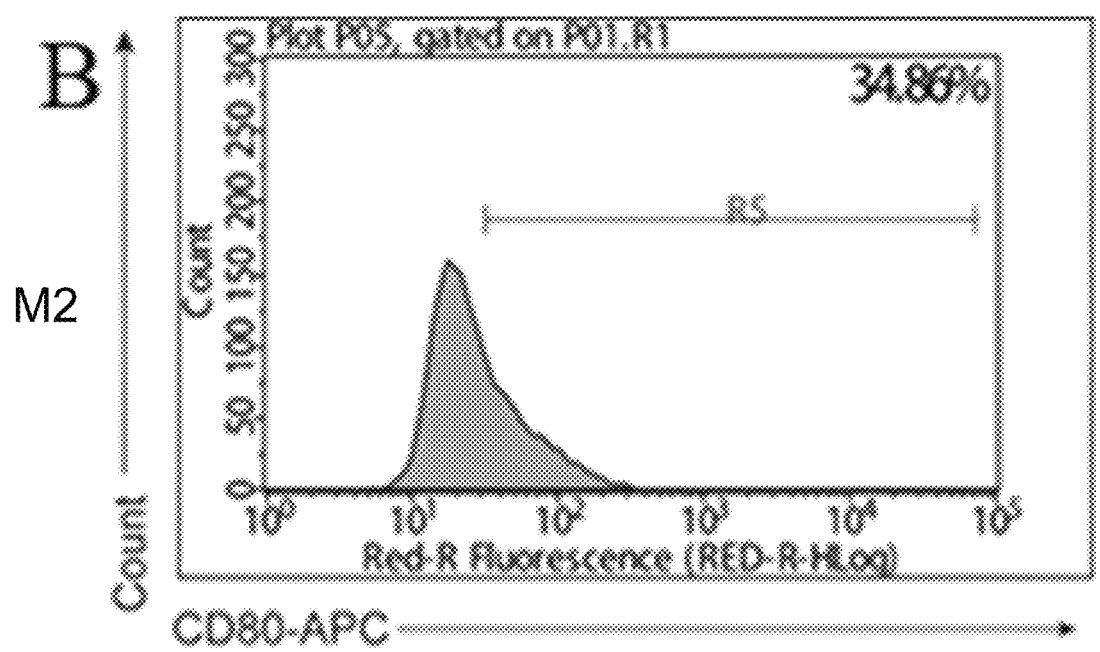
FIG. 12B is a diagram illustrating flow cytometry analysis of the expression of CD80 of M2 macrophages according to some embodiments of the present disclosure.
Figure 12C:
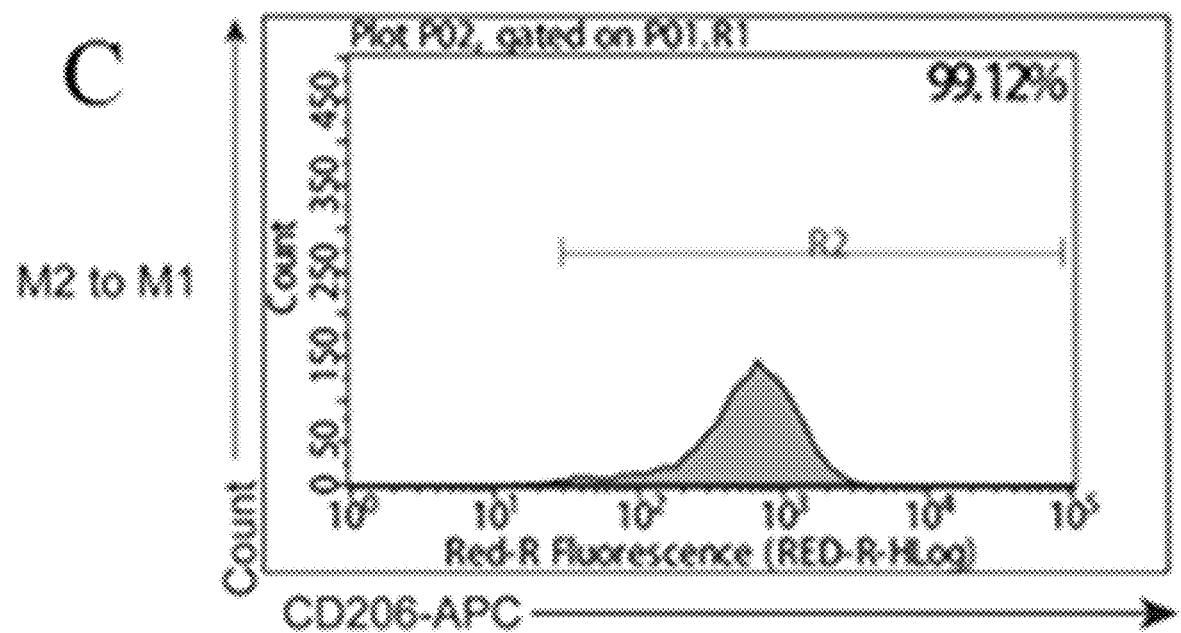
FIG. 12C is a diagram illustrating flow cytometry analysis of the expression of CD206 for transformation of M2 macrophages to M1 macrophages according to some embodiments of the present disclosure.
Figure 12D:
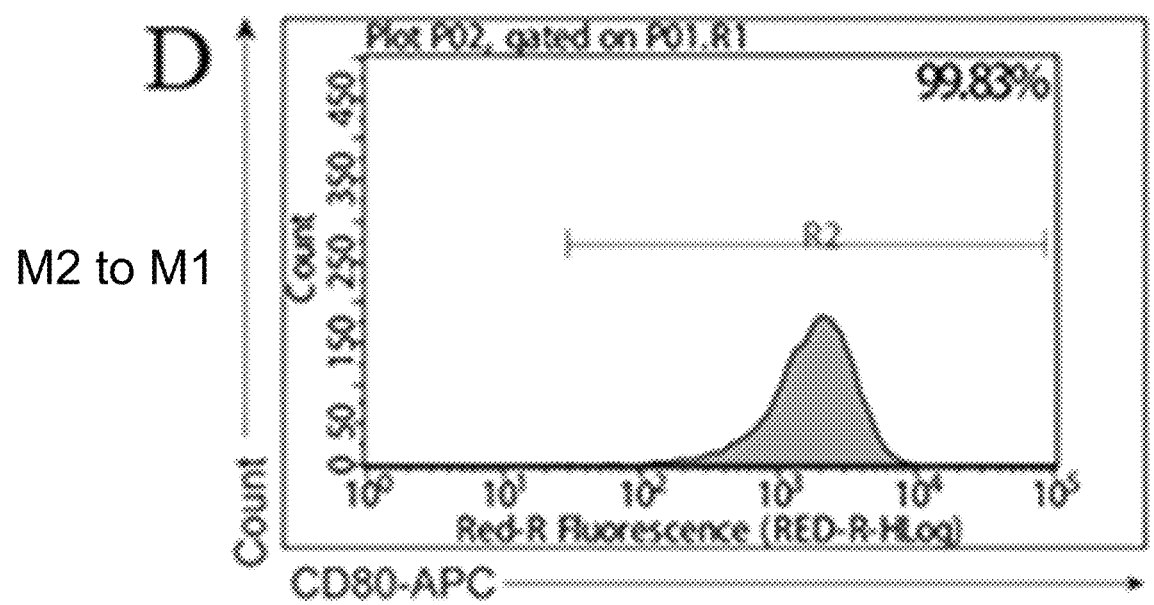
FIG. 12D is a diagram illustrating flow cytometry analysis of the expression of CD80 for transformation of M2 macrophages to M1 macrophages according to some embodiments of the present disclosure.

The obtained M2 macrophages by polarization were transformed into M1 macrophages. The suction device sucked off the old liquid, M7 medium was added, and the cells were incubated in the constant temperature incubator with 5% $CO_2$ at 37° C. for 2 days to obtain M1 macrophages. The cell morphology during the transformation of M2 macrophages to M1 macrophages is shown in FIG. 11. The flow cytometry was performed on M2 macrophages transforming to M1 macrophages to detect CD80 and CD206 expression (shown in FIGS. 12A-12D).

2. Flow Cytometry of Suspended Cells

The specific experimental steps for the flow cytometry of suspension cells were as follows:

(1) The supernatant was transferred to 15 mL centrifuge tube for centrifuging at 250 g for 5 min to remove the supernatant.

(2) 1 mL DPBS was added to wash the cells once.

(3) Cells were resuspended with 100 μL DPBS containing 4% FBS.

(4) The appropriate flow cytometry antibody was added and incubated at 4° C. for 30 min.

(5) The supernatant was removed by centrifugation at 250 g, and 1 mL DPBS was added to wash the cells three times.

(6) the cells were resuspended with 200 μL DPBS and proceeded to the flow cytometer for detection.

3. Experimental Results

The cell morphology of iPSC cells of this example under the 4× optical microscope is shown in FIG. 1, and it can be seen from FIG. 1 that the iPSC cells start to enter the differentiation when the iPSC confluence reaches 70%-80%.

The cell morphologies of cells on day 0, day 4, day 12, day 19, day 26, and day 33 during the differentiation process under the 4× optical microscope are shown in the FIG. 2. It can be seen from FIG. 2 that relatively homogeneous EBs are formed on day 0 of differentiation, EBs appear different sizes of cavities on day 4 of differentiation, the suspended cells begin to appear on the day 12 of differentiation, the suspended cells increase continuously on day 19 of differentiation to form cell colonies, the cells present a larger foamy morphology on day 26 of differentiation, and the cells mostly present wall-adherent short fibers and some other cells present a slightly circularadherent state on day 33 of differentiation.

Figure 3:
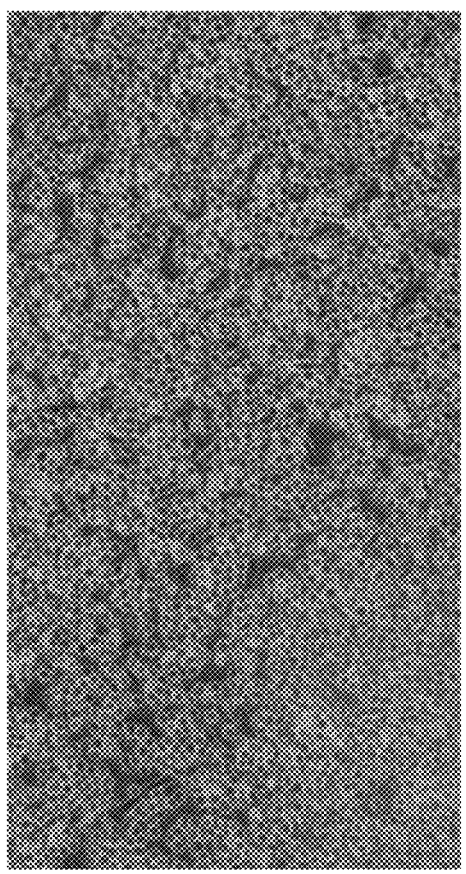
FIG. 3 is a cell morphology image of M1 macrophages and M2 macrophages according to some embodiments of the present disclosure.
Figure 3:
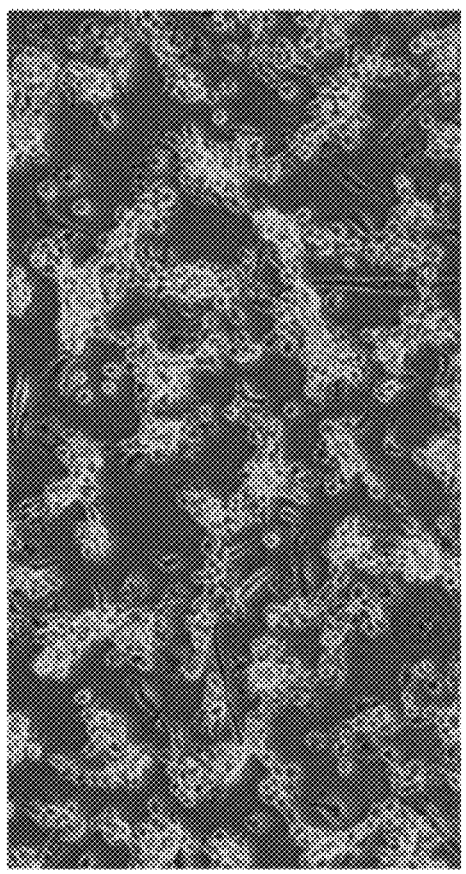

The morphology of M1 macrophages and M2 macrophages in this example is shown in FIG. 3. It can be seen from FIG. 3 that the M1 macrophages present a polygonal fibrous morphology and grow in colonies, the M2 macrophages are mostly in the form of semi-adherent circular morphology, and some M2 macrophages present short fiber shape.

Figure 4:
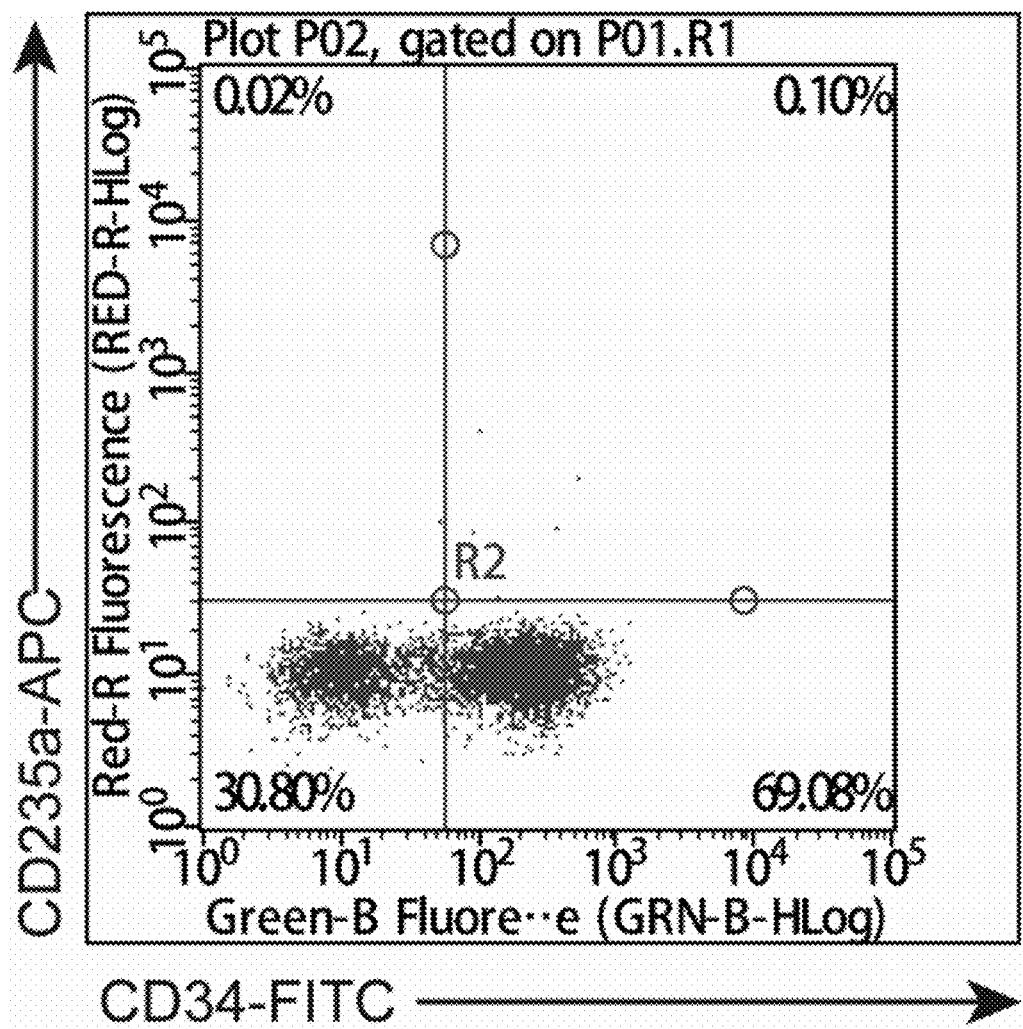
FIG. 4 is a detection diagram illustrating the expression of CD34 and CD235a on day 4 of differentiation according to some embodiments of the present disclosure.
Figure 5A:
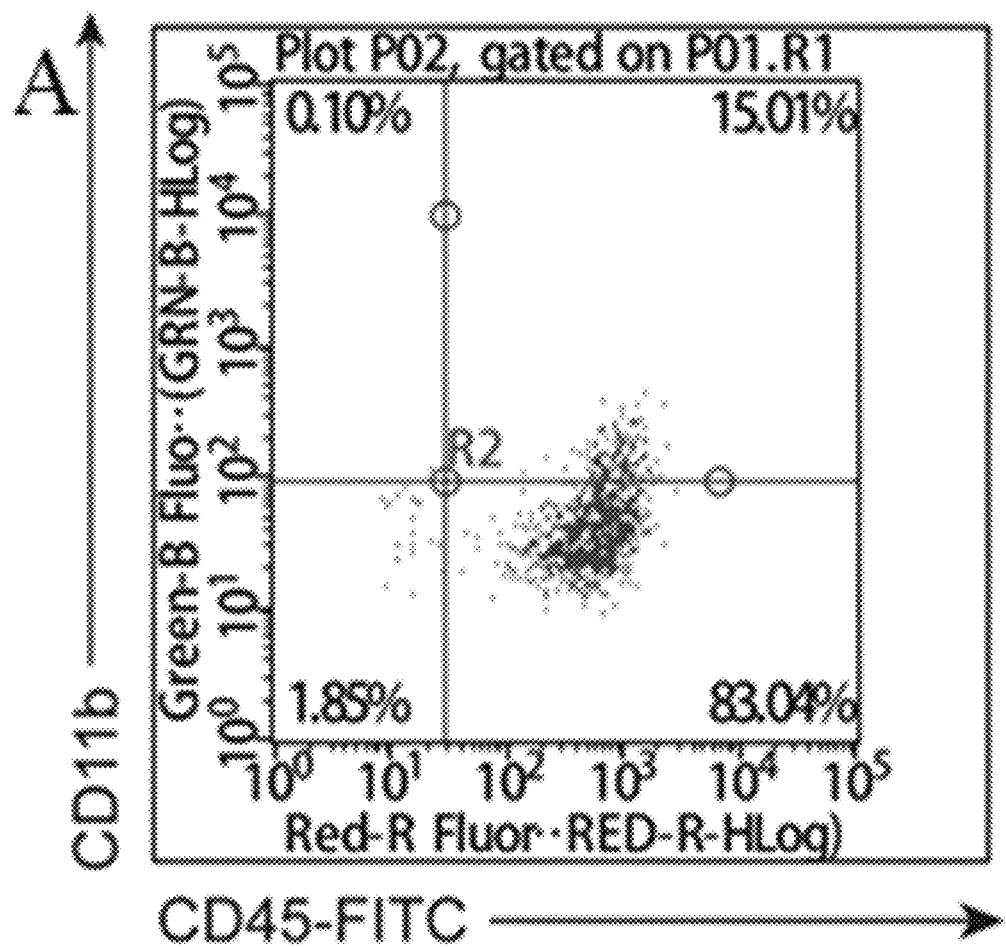
FIG. 5A is a detection diagram of the expression of CD45 and CD11b on day 12 of differentiation according to some embodiments of the present disclosure.
Figure 5B:
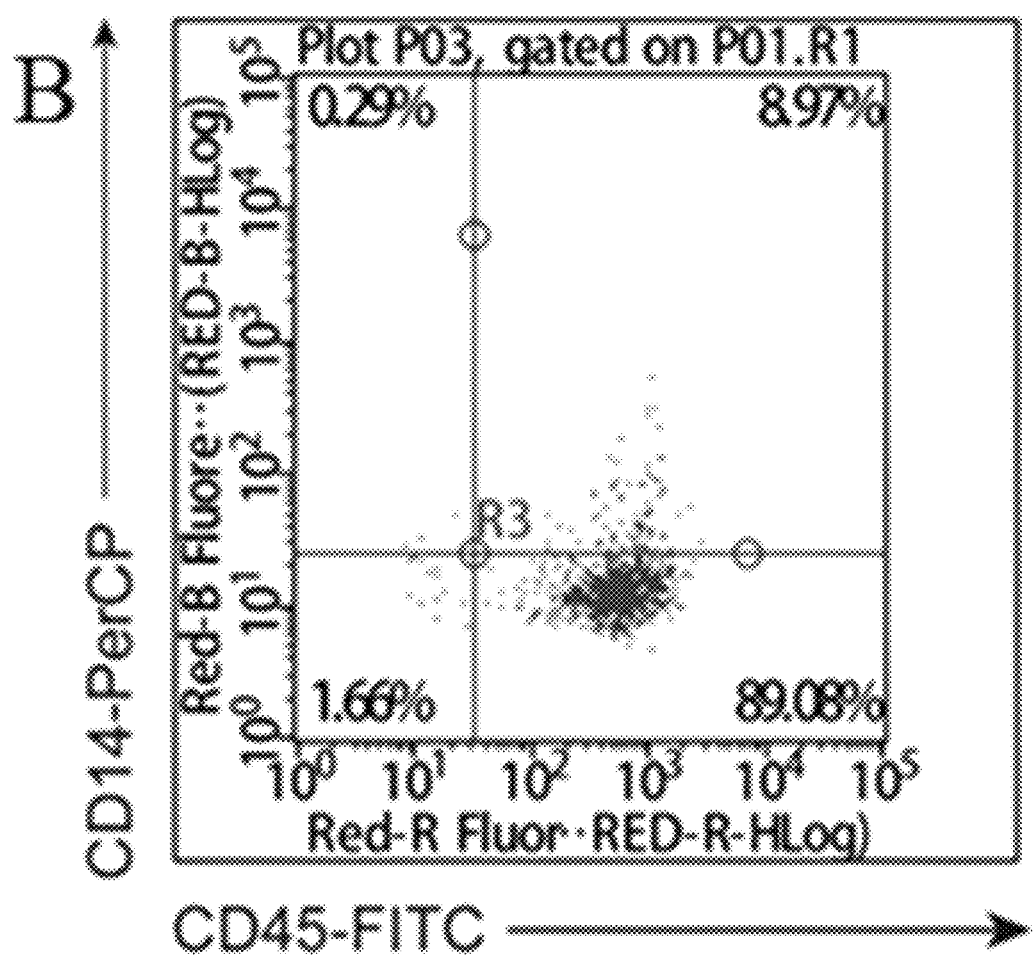
FIG. 5B is a detection diagram of the expression of CD45 and CD14 on day 12 of differentiation according to some embodiments of the present disclosure.

Expression of CD34 and CD235a on day 4 of differentiation in this example is shown in FIG. 4. It can be seen from FIG. 4 that on day 4 of differentiation, CD235a is not expressed, and there are approximately 69% CD34+ cells, indicating that the ratio of hemogenic endothelial cells is close to 70% at this time.

Expression of CD45, CD14, and CD11b on day 12 of differentiation of this example is shown in FIGS. 5A and 5B. It can be seen from FIGS. 5A-5B that on day 12 of differentiation, about 98% of the suspended cells express CD45, about 15% of cells express CD11b, and about 9% of cells express CD14, indicating that the hematopoietic progenitor cell rate reaches 98% and the hematopoietic progenitor cells begin to differentiate to monocytes on day 12 of differentiation.

Expression of CD45, CD14, and CD11b on day 19 of differentiation of this example is shown in FIGS. 6A and 6B. It can be seen from FIGS. 6A-6B that on day 19 of differentiation, about 94% of the suspended cells express CD45, about 87% of cells express CD11b, and about 73% of cells express CD14, indicating that the monocyte rate on day 19 of differentiation may reach 73%.

Figure 7A:
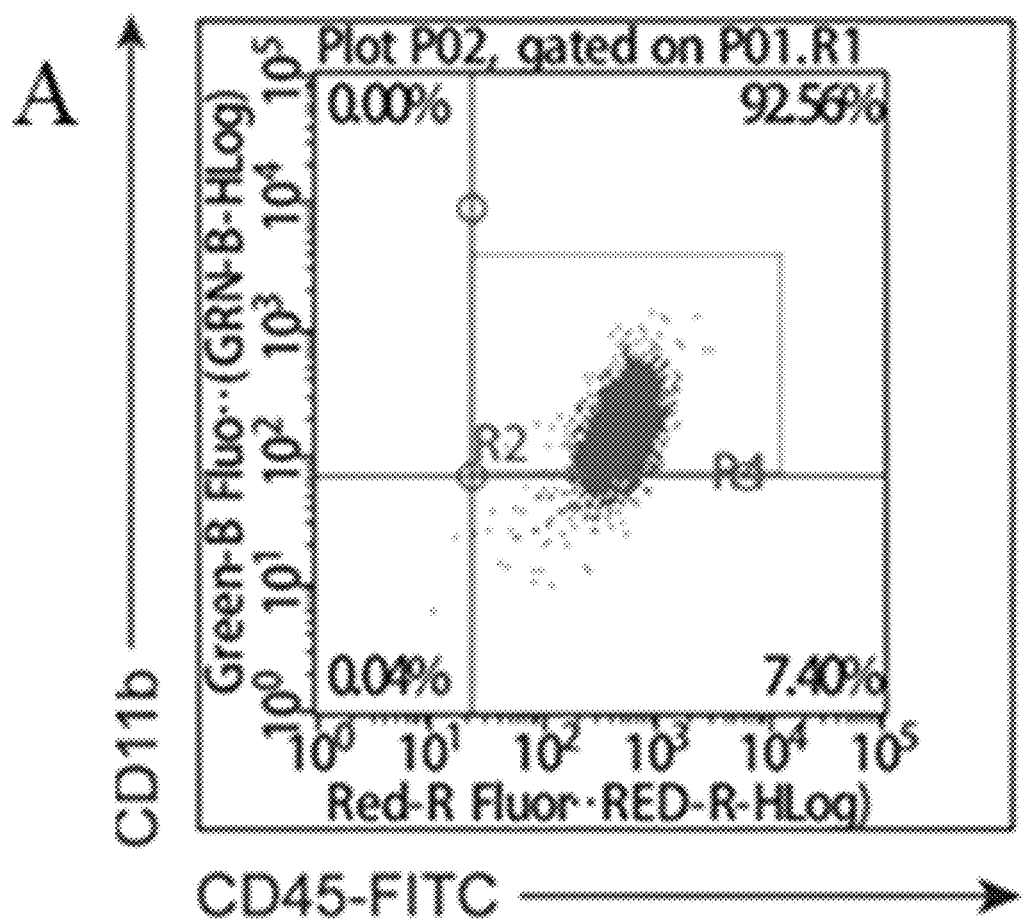
FIG. 7A is a detection diagram of the expression of CD45 and CD11b on day 26 of differentiation according to some embodiments of the present disclosure.
Figure 7B:
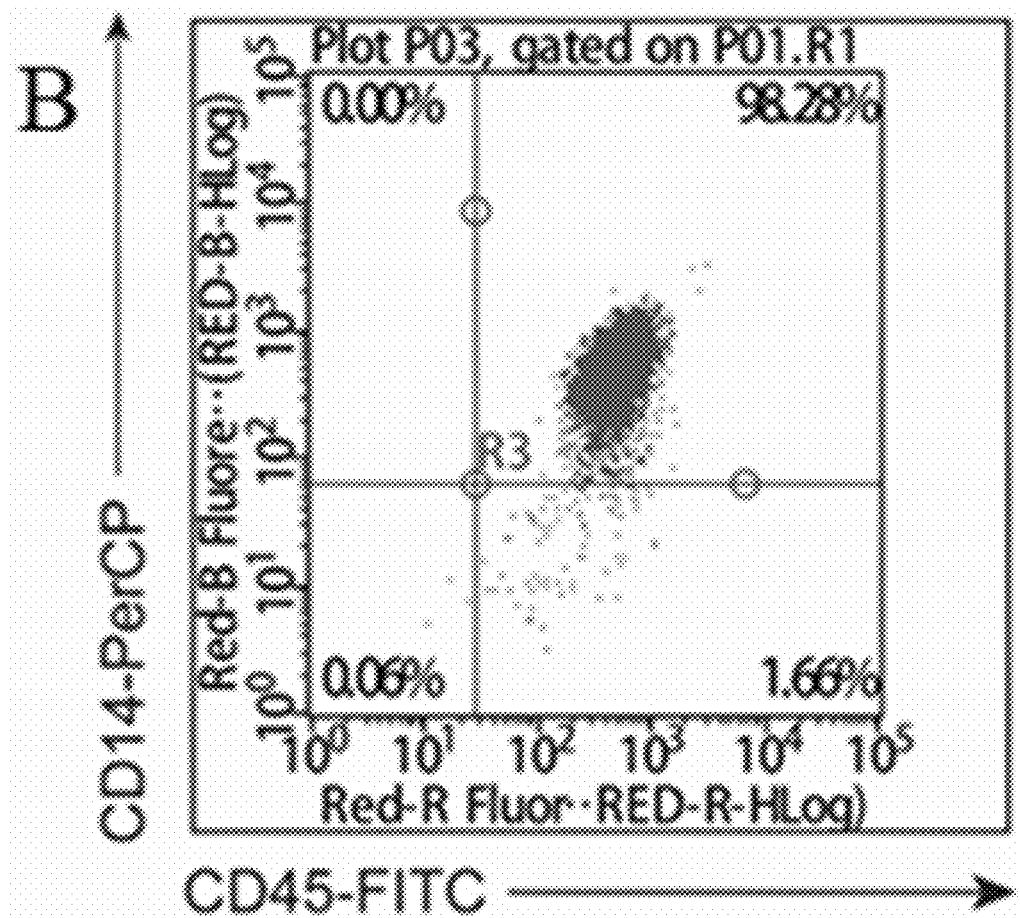
FIG. 7B is a detection diagram of the expression of CD45 and CD14 on day 26 of differentiation according to some embodiments of the present disclosure.
Figure 8:
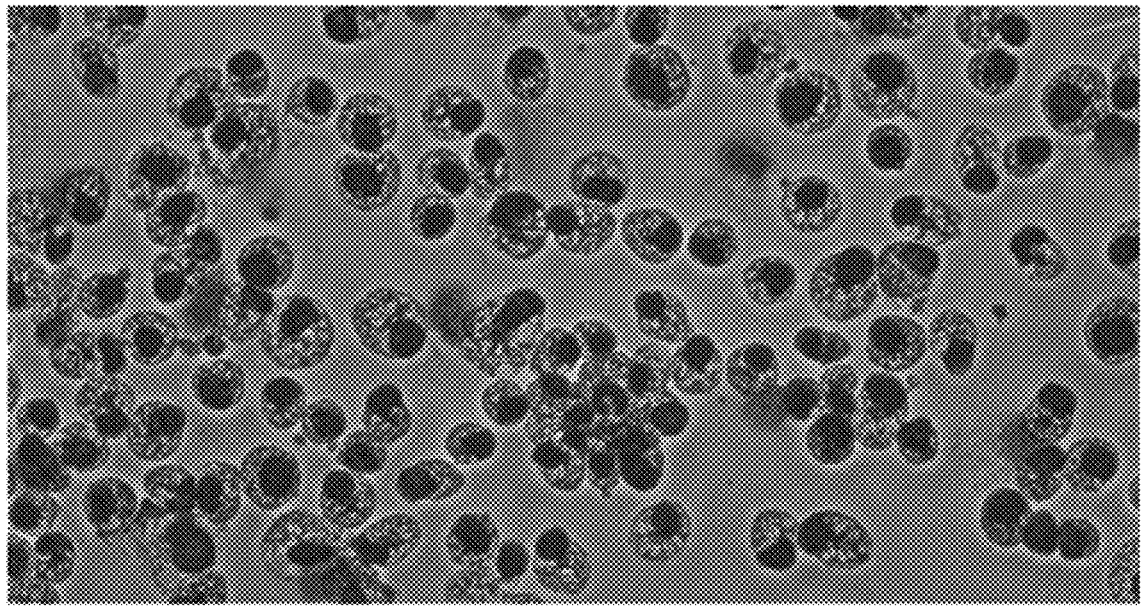
FIG. 8 is a Giemsa staining image of cells on day 26 of differentiation according to some embodiments of the present disclosure.

Expression of CD45, CD14, and CD11b on day 26 of differentiation of this example is shown in FIGS. 7A and 7B. It can be seen from FIGS. 7A and 7B that on day 26 of differentiation, about 99.96% of the suspended cells express CD45, about 92.5% of cells express CD11b, and about 98.3% of cells express CD14. The detection result of Giemsa staining of cells on the 26th day of differentiation of this example is shown in FIG. 8. It can be seen from FIG. 8 that the cells present a single nucleus morphology. At this point, the monocyte ratio is close to 100%. At this point, each IPSC may produce about 100,000 monocytes.

Figure 14:
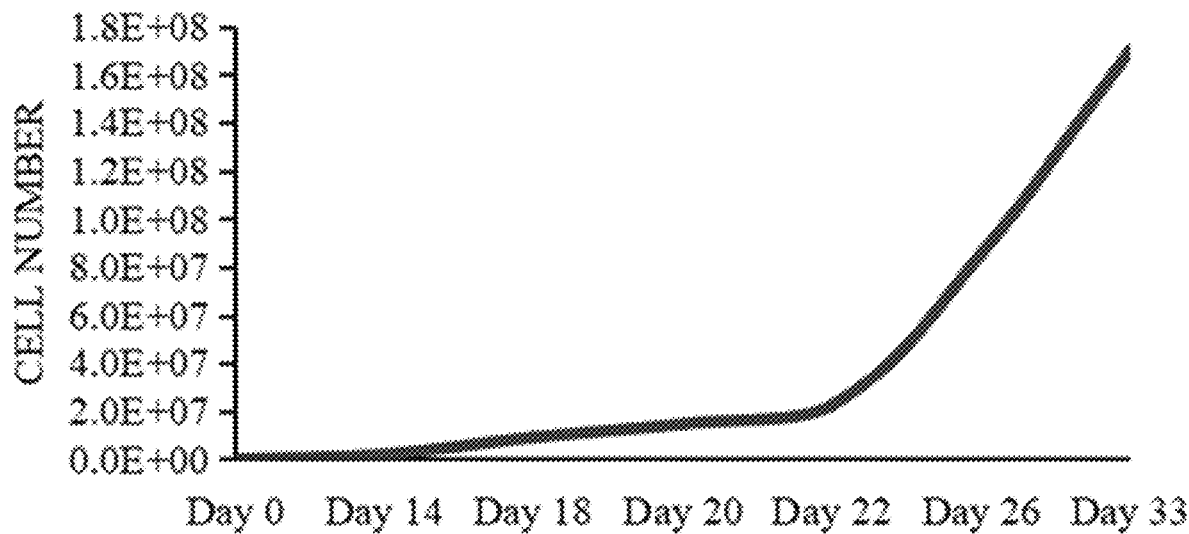
FIG. 14 is a cell yield graph of macrophages according to some embodiments of the present disclosure.

Expression of CD45, CD14, and CD11b on day 33 of differentiation of this example is shown in FIGS. 9A and 9B. It can be seen from FIGS. 9A and 9B that on day 33 of differentiation, about 98% of the suspended cells express CD45, about 100% of cells express CD11b, and about 97.6% of cells express CD14. At this time, the macrophage rate reaches 100%, and each IPSC may produce about 188,000 macrophages, as shown in FIG. 14.

Expression of CD206 and CD80 in polarized M1 macrophages and polarized M2 macrophages of this example is shown in FIGS. 10A-10D. It can be seen from FIGS. 10A-10D that M1 macrophages have about 99.62% of CD80+ cells after polarization, indicating that the polarization rate of M1 macrophages may reach more than 99%.

M2 macrophages have about 99.62% of CD206+ cells after polarization, and the fluorescence intensity of CD206 is stronger than that of M1 macrophages, indicating that the polarization rate of M2 macrophages may reach more than 99%.

The cell morphology of M2 macrophages transforming to M1 macrophages in this example is shown in FIG. 11. It can be seen from FIG. 11 that the M2 macrophages present semi-adherent circular or adherent short spindle shapes (left) before polarization, and the M1 macrophages present polygonal fibrous or long-fibrous shapes after the transformation of M2 macrophages to the M1 macrophages and the cells present colony growth (right).

CD80 and CD206 expression of M2 macrophages transforming to M1 macrophages of this example is shown in FIGS. 12A-12D. It can be seen from FIGS. 12A-12D that there is about 99.62% CD206+ cells and 34.86% CD80+ cells before the transformation of M2 macrophages to M1 macrophages; after the transformation of M2 macrophages to M1 macrophages, there is about 99.12% CD206+ cells, but the fluorescence intensity of CD206 is weaken compared with that of M2 macrophages, at this time, the proportion of CD80+ cells reaches 99.83%, indicating that the transformation rate of M2 macrophages to M1 macrophages is high.

Example 2 Validation of Phagocytosis of M2 Macrophages

The M2 macrophages prepared in Example 1 were counted, LnCap cells were spread into a 12-well plate at $4\times10^4/cm^2$ 12 h in advance and the GFP-labeled LnCap cells were counted after 12 h, and ⅕ of the LnCap cells were co-cultured with M2 macrophages in the constant temperature incubator with 5% $CO_2$ at 37° C. for 2 h. After gently blowing to remove LnCap cells, the macrophages were digested into single cells. The cells were washed once with DPBS, and 200 μL of DPBS containing 4% serum was added to resuspend the cells, then 5 μL of CD206-APC antibody (purchased from Shanghai Ziqi Biotechnology Co., Ltd.) was added, and the cells were incubated at 4° C. for 30 min.

Figure 13:
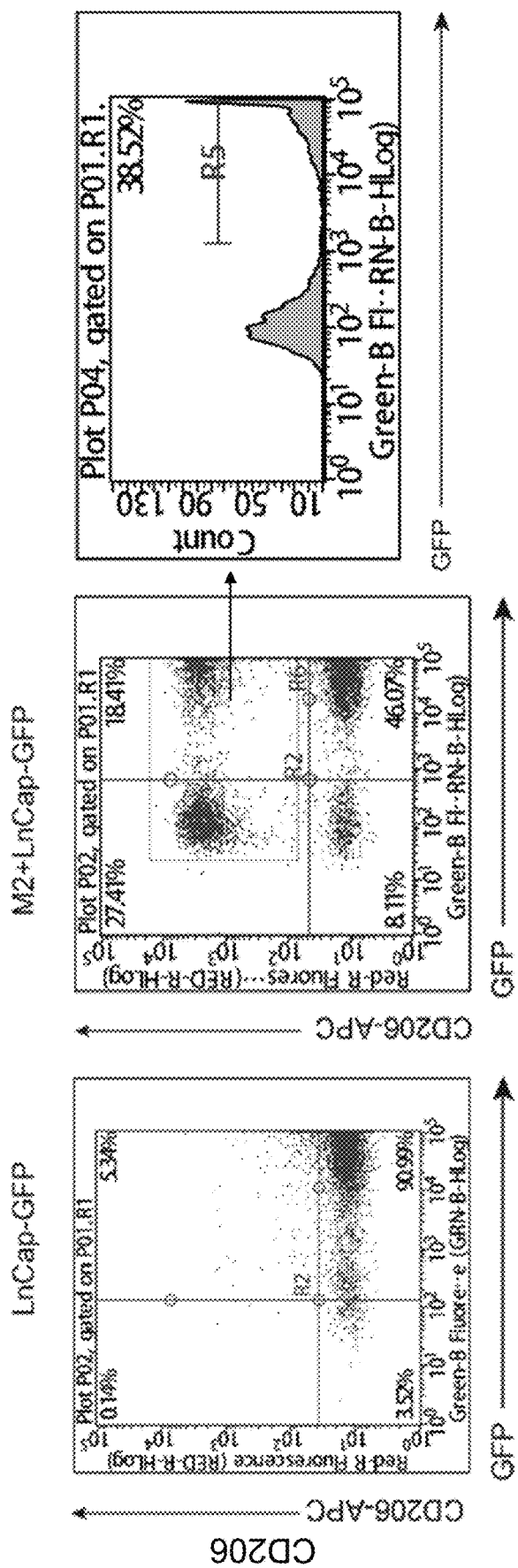
FIG. 13 is a diagram illustrating phagocytosis assay validation of M2 macrophages obtained by polarization according to some embodiments of the present disclosure.

The cells were subsequently washed 3 times with DPBS, and finally resuspended with 200 μL of DPBS for flow cytometry, which is detailed in Example 1, and the results are shown in FIG. 13. As shown in FIG. 13, the flow cytometry result indicates that LnCap-GFP cells do not express CD206 (left) and CD206 and GFP double-positive cells appear after co-incubation of M2 macrophages and LnCap-GFP (middle). It reveals that about 38.5% of macrophages have phagocytosis (right) by further analysis of the ratio of CD206+ cells and CD206+/GFP+ cells.

While embodiments of the present disclosure have been shown and described above, it is to be understood that the above embodiments are exemplary and are not to be construed as a limitation of the present disclosure, and that a person of ordinary skill in the art, within the context of the present disclosure, may make changes, modifications, substitutions and variations.

What is claimed is:

1. A kit for inducing induced Pluripotent Stem Cells (iPSC) differentiation to obtain macrophages, comprising: a first stage medium, a second stage medium, a third stage medium, a fourth stage medium, a fifth stage medium, and a sixth stage medium; wherein
the first stage medium is an iPSC culture medium containing a ROCK pathway inhibitor and polyvinyl alcohol, the second stage medium is an iPSC culture medium containing a GSK-3B inhibitor, the third stage medium comprises an M1 medium and an M2 medium, the fourth stage medium is an M3 medium, the fifth stage medium is an M4 medium, and the sixth stage medium is an M5 medium;
the M1 medium comprises a serum-free hematopoietic cells culture medium, DMEM/F12, L-glutamine, ascorbic acid, Insulin-Transferrin-Selenium-Ethanolamine, BMP4, VEGF, and bFGF;
the M2 medium comprises the M1 medium and inhibitors of TGF—B type I receptors ALK5, ALK4, and ALK7;
the M3 medium comprises macrophage medium, L-glutamine, ascorbic acid, Insulin-Transferrin-Selenium-Ethanolamine, non-essential amino acids (NEAA), β-mercaptoethanol, BMP4, VEGF, bFGF, SCF, IL-3, and M-CSF;
the M4 medium comprises macrophage medium, L-glutamine, ascorbic acid, Insulin-Transferrin-Selenium-Ethanolamine, NEAA, β-mercaptoethanol, IL-3, and M-CSF;
the M5 medium comprises macrophage medium, L-glutamine, ascorbic acid, Insulin-Transferrin-Selenium-Ethanolamine, NEAA, β-mercaptoethanol, and M-CSF;
the ROCK pathway inhibitor in the first stage medium is selected from the group consisting of Y-27632, Thiazovivin, Fasudil (HA-1077) HCl, GSK429286A, RKI-1447, and Azaindole 1;
the GSK-3β inhibitor in the second stage medium is selected from the group consisting of CHIR-99021, SB216763, CHIR-98014, TWS119, Tideglusib, and SB415286; and
the inhibitors of the TGF-β type I receptors ALK5, ALK4, and ALK7 in the M2 medium is selected from the group consisting of SB431542, Galunisertib (LY2157299), LY2109761, SB525334, SB505124, and GW788388.

2. The kit of claim 1, wherein
a concentration of Y-27632 in the first stage medium is within a range of 0.5-20 μM;
a concentration of CHIR-99021 in the second stage medium is within a range of 1-10 μM;
in the third stage medium, the M1 medium comprises 50 wt % serum-free hematopoietic cells culture medium, 50 wt % DMEM/F12, 1 wt % L-glutamine, 50 μg/mL ascorbic acid, 1×Insulin-Transferrin-Selenium-Ethanolamine, 50 μg/mL BMP4, 50 μg/mL VEGF, and 50 μg/mL bFGF, and the M2 medium comprises the M1 medium and 1-9 UM SB431542;
in the fourth stage medium, the M3 medium comprises macrophage medium, 1 wt % L-glutamine, 50 μg/mL ascorbic acid, 1×Insulin-Transferrin-Selenium-Ethanolamine, 1×NEAA, 55 UM β-mercaptoethanol, 50 μg/mL BMP4, 50 μg/mL VEGF, 50 μg/mL bFGF, 50 g/mL SCF, 25 μg/mL IL-3, and 100 μg/mL M-CSF;
in the fifth stage medium, the M4 medium comprises macrophage medium, 1 wt % L-Glutamine, 50 μg/mL Ascorbic Acid, 1×Insulin-Transferrin-Selenium-Ethanolamine, 1×NEAA, 55 UM β-mercaptoethanol, 25 μg/mL IL-3, and 100 μg/mL M-CSF;
in the sixth stage medium, the M5 medium comprises macrophage medium, 1 wt % L-glutamine, 50 μg/mL ascorbic acid, 1×Insulin-Transferrin-Selenium-Ethanolamine, 1×NEAA, 55 UM β-mercaptoethanol, and 100 μg/mL M-CSF.

3. The kit of claim 1, further comprising a seventh stage medium, wherein the seventh stage medium comprises M6 medium or M7 medium;
the M6 medium comprises macrophage medium, 1 wt % L-glutamine, 50 μg/mL ascorbic acid, 1×Insulin-Transferrin-Selenium-Ethanolamine, 1×NEAA, 55 UM β-mercaptoethanol, 20 μg/mL IFN-γ, and 50 μg/mL LPS;
the M7 medium comprises macrophage medium, 1 wt % L-glutamine, 50 μg/mL ascorbic acid, 1×Insulin-Transferrin-Selenium-Ethanolamine, 1×NEAA, 55 UM β-mercaptoethanol, 20 μg/mL IL-4, and 20 μg/mL IL-13.

* * * * *